(12) United States Patent
Fujie

(10) Patent No.: US 8,852,293 B2
(45) Date of Patent: Oct. 7, 2014

(54) COMPOUND HAVING TRIAZINE SIDE CHAIN, COLORING COMPOSITION, INKJET INK, INKJET RECORDING METHOD, COLOR FILTER, AND COLOR TONER

(71) Applicant: FUJIFILM Corporation, Tokyo (JP)

(72) Inventor: Yoshihiko Fujie, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/189,114

(22) Filed: Feb. 25, 2014

(65) Prior Publication Data

US 2014/0170538 A1    Jun. 19, 2014

Related U.S. Application Data

(63) Continuation of application No. PCT/JP2012/068597, filed on Jul. 23, 2012.

(30) Foreign Application Priority Data

Aug. 30, 2011 (JP) .................................. 2011-188043

(51) Int. Cl.

| | |
|---|---|
| C09B 67/10 | (2006.01) |
| C09D 11/00 | (2014.01) |
| G02B 5/20 | (2006.01) |
| C09D 11/328 | (2014.01) |
| C09B 11/28 | (2006.01) |
| G03G 9/09 | (2006.01) |

(52) U.S. Cl.
CPC . *C09B 11/28* (2013.01); *G02B 5/20* (2013.01); *C09D 11/328* (2013.01); *G03G 9/0924* (2013.01)
USPC ....... 8/637.1; 8/565; 8/566; 8/587; 106/31.13

(58) Field of Classification Search
USPC ................. 8/637.1, 565, 566, 587; 106/31.13
See application file for complete search history.

(56) References Cited

U.S. PATENT DOCUMENTS

| 5,798,276 A | 8/1998 | Haugland et al. |
|---|---|---|
| 2003/0095169 A1 | 5/2003 | Ito et al. |

FOREIGN PATENT DOCUMENTS

| EP | 1564258 A1 * | 8/2005 | ............ C09B 11/24 |
|---|---|---|---|
| JP | 60-156762 A | 8/1985 | |
| JP | 9-157562 A | 6/1997 | |
| JP | 2002-201377 A | 7/2002 | |
| JP | 2003-160749 A | 6/2003 | |
| JP | 2004-224949 A | 8/2004 | |
| JP | 2007-131832 A | 5/2007 | |
| JP | 2010-32999 A | 2/2010 | |
| JP | 2010-244027 A | 10/2010 | |
| JP | 2010-286847 A | 12/2010 | |
| JP | 2011-118365 A | 6/2011 | |

OTHER PUBLICATIONS

STIC Search Report dated May 21, 2014.*
Written Opinion for PCT/JP2012/068597 dated Sep. 11, 2012 [PCT/ISA/237].
Notification of Transmittal of translation of the International Preliminary Report on Patentability for PCT/JP2012/068597 dated Mar. 13, 2014 [PCT/IB/338].
International Preliminary Report on Patentability for PCT/JP2012/068597 dated Mar. 4, 2014 [PCT/IB/373].
International Search Report (PCT/ISA/210), dated Sep. 11, 2012, issued by the International Searching Authority in counterpart International Patent Application No. PCT/JP2012/068597.
Written Opinion (PCT/ISA/237), dated Sep. 11, 2012, issued by the International Searching Authority in counterpart International Patent Application No. PCT/JP2012/068597.

* cited by examiner

*Primary Examiner* — Eisa Elhilo
(74) *Attorney, Agent, or Firm* — Sughrue Mion, PLLC

(57) ABSTRACT

There is provided a compound represented by Formula (1), and a coloring composition including the compound:

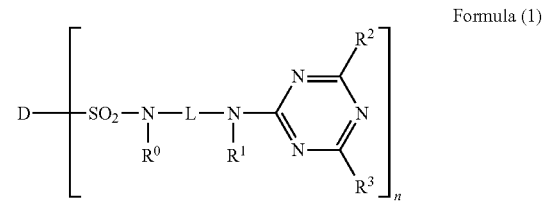

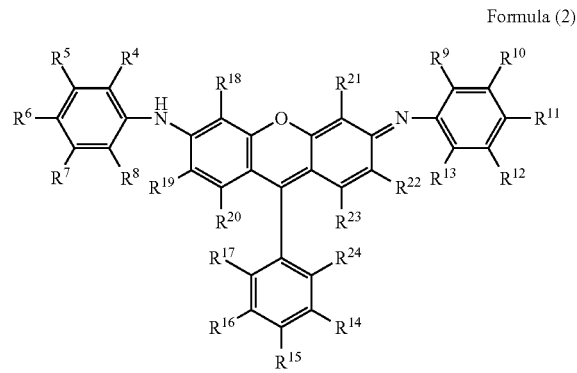

wherein, in Formula (1), $R^0$ to $R^3$ each independently represent a hydrogen atom or a substituent, and $R^0$ and $R^1$, $R^0$ and L, or $R^1$ and L may be combined with each other to form a ring, L represents a single bond or a divalent linking group, D represents a residue in which n hydrogen atoms are removed from a compound represented by Formula (2), n represents an integer of 1 or more, provided that when n represents an integer of 2 or more, a plurality of $R^0$'s to $R^3$'s and L's may be the same or different, the compound represented by Formula (1) has at least one ionic hydrophilic group, and
in Formula (2), $R^4$ to $R^{24}$ each independently represent a hydrogen atom or a substituent.

11 Claims, No Drawings

COMPOUND HAVING TRIAZINE SIDE CHAIN, COLORING COMPOSITION, INKJET INK, INKJET RECORDING METHOD, COLOR FILTER, AND COLOR TONER

CROSS-REFERENCE TO RELATED APPLICATIONS

This application is a continuation of PCT international Application No. PCT/JP2012/068597, filed on Jul. 23, 2012, which claims priority under 35 U.S.C. §119(a) to Japanese Patent Application No. 2011-188043 filed on Aug. 30, 2011, all of which are hereby incorporated by reference into the present application.

TECHNICAL FIELD

The present invention relates to a novel compound having a triazine side chain, a coloring composition including the corresponding compound, an inkjet ink, an inkjet recording method, a color filter and a color toner.

BACKGROUND ART

An inkjet recording method is a method of performing printing by jetting and attaching small liquid drops of ink to a recording medium such as paper, as well-known in the art. By this printing method, it is possible to print a high-resolution and high-quality image conveniently at a high speed with an inexpensive apparatus, and particularly in color printing, technology development has been recently conducted as an image forming method which may replace photographs.

When a color image is formed using an inkjet recording method, it is common to use at least a yellow ink, a magenta ink, a cyan ink and a black ink. In the related art, water-based ink is usually used as the inkjet ink in terms of safety such as malodor and hazard associated with fire-fighting. This ink is required to fall within suitable ranges in physical property values such as viscosity, surface tension and the like, to be excellent in storage stability and preventing clogging of a nozzle, to impart a recording image at a high concentration, and to be excellent in light fastness, ozone resistance, water resistance and moisture resistance.

Such a performance is mostly satisfied by using a water-based ink containing water or a mixture solution of water and a water-soluble organic solvent as a main solvent, but color tone, clearness, light fastness, ozone resistance, water resistance, moisture resistance and the like are influenced considerably by coloring agents, and various dyes have been studied in the related art.

In particular, in a color recording method using a plurality of color inks, uniform characteristics are required for all the constituting inks. Among them, a magenta dye has a problem in that discoloration by ozone or light (sunlight, fluorescent light and the like) or change in color tone occurs significantly, as compared to other dyes to cyan dye and a yellow dye). Accordingly, when ozone resistance or light fastness of the magenta ink is inferior to that of other inks, discoloration of the magenta ink causes the color tone of the whole image of printed matters to be changed, resulting in deteriorating the quality.

In the related art, an acidic dye having good chromogentic property and high water solubility, for example, C. I. Acid Red 52, 249 and 289 is known as a magenta dye for inkjet, but when such a dye is used alone, clogging of a nozzle hardly occurs due to the high water solubility, but the performances of the ozone resistance, light fastness and moisture resistance are very low.

Accordingly, Patent Document 1 discloses a magenta dye ink, which is excellent in light fastness, water resistance, color tone, clogging reliability and the like by using a magenta dye having a triazine side chain with a specific structure.

Further, Patent Document 2 discloses an inkjet recording liquid of a magenta color, which uses, as a colorant, a xanthene derivative substituted with an amino group which may have a substituent, and describes that due to excellent light fastness of the color image, color tone for good color reproducibility is excellent.

CITATION LIST

Patent Document

Patent Document 1: Japanese Patent Application Laid-Open No. 2003-160749

Patent Document 2: Japanese Patent Application Laid-Open No. H9-157562

DISCLOSURE OF INVENTION

Problems to be Solved by Invention

However, the colorants described in Patent Documents 1 and 2 need to be much further improved in performances (for example, ozone resistance, light fastness and moisture resistance) in use as an inkjet ink, and accordingly, there is still room for review.

An object of the present invention is to provide a colorant, which has further improvements in image fastness including ozone resistance, light fastness and moisture resistance, and imparts a printed matter which is excellent in print concentration.

Means for Solving the Problems

As a result of intensive studies considering the aforementioned problems, the present inventors have found that a novel compound, in which a triazine unit having a specific linking group is introduced into a side chain thereof, and having a specific structure derived from a xanthene structure further improves performances according to image fastness such as ozone resistance, light fastness and moisture resistance of a printed matter, and imparts a printed matter which is excellent in print concentration, thereby completing the present invention.

That is, the present invention is as follows.

[1] A coloring composition containing a compound represented by Formula (1).

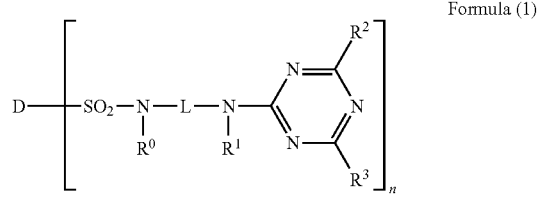

Formula (1)

-continued

Formula (2)

In Formula (1), $R^0$ to $R^3$ each independently represent a hydrogen atom or a substituent. $R^0$ and $R^1$, $R^0$ and L, or $R^1$ and L may be combined with each other to form a ring.

L represents a single bond or a divalent linking group.

D represents a residue in which n hydrogen atoms are removed from a compound represented by Formula (2).

n represents an integer of 1 or more. However, when a represents an integer of 2 or more, a plurality of $R^0$'s to $R^3$'s and L's may be the same or different.

In Formula (2), $R^4$ to $R^{24}$ each independently represent a hydrogen atom or a substituent.

However, the compound represented h Formula (1) has at least one ionic hydrophilic group.

[2] The coloring composition described in [1], in which in Formula (2), $R^4$, $R^8$, $R^9$ and $R^{13}$ each independently represent a hydrogen atom or an aliphatic group.

[3] The coloring composition described in [1] or [2], in which in Formula (2), $R^5$ to $R^7$, $R^{10}$ to $R^{12}$ and $R^{14}$ to $R^{23}$ represent a hydrogen atom.

[4] The coloring composition described in [3], in which in Formula (2), $R^{24}$ represents a hydrogen atom or an ionic hydrophilic group, and D in Formula (1) represents a residue in which n hydrogen atoms are removed from hydrogen atoms as $R^5$ to $R^7$, $R^{10}$ to $R^{12}$ and $R^{24}$ of the compound represented by Formula (2). However, n represents an integer of 1 to 7.

[5] The coloring composition described in any one of [1] to [4], in which L in Formula (1) represents an alkylene group having 1 to 10 carbon atoms, which may have a substituent.

[6] An inkjet ink containing the coloring composition described in any one of [1] to [5].

[7] An inkjet recording method including forming an image by using the coloring composition described in any one of [1] to [5] or the inkjet ink described in [6].

[8] A color filter containing the compound represented by Formula (1) described in any one of [1] to [5].

[9] A color toner containing the compound represented by Formula (1) described in any one of [1] to [5].

[10] A compound represented by Formula (1).

Formula (1)

Effects of the Invention

According to the present invention, provided are a novel compound having a specific triazine unit in a side chain thereof and having a specific structure derived from a xanthene structure, in which performances according to image fastness such as ozone resistance, light fastness and moisture resistance of a printed matter are further improved than those in the related art, and a primed matter having excellent print concentration is imparted, a coloring composition containing the corresponding compound, an inkjet ink, and an inkjet recording method.

Further, provided are a color filter and a color toner, which contain the novel compound.

EMBODIMENTS FOR CARRYING OUT THE INVENTION

Hereinafter, the present invention will be described in detail.

First, in the present invention, Group A of substituents and an ionic hydrophilic group will be defined.

(Group A of Substituents)

Examples of Group A of substituents include a halogen atom, an alkyl group, an aralkyl group, an alkenyl group, an alkynyl group, an aryl group, a heterocyclic group, a cyano group, a hydroxyl group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, an acyl group, an aryloxycarbonyl group, an alkoxycarbonyl group, a carbamoyl group, an aryl or heterocyclicazo group, an imide group, a phosphino group, a phosphinyl group, a phosphinyloxy group, a phosphinylamino group, a silyl group, and an ionic hydrophilic group. These substituents may be further substituted, and examples of a further substituted substituent include a group selected from Group A of substituents as described above.

More specifically, examples of the halogen a include a fluorine atom, a chlorine atom, a bromine atom or an iodine atom.

Examples of the alkyl group include a straight, branched or cyclic, substituted or unsubstituted alkyl group, and also include a cycloalkyl group, a bicycloalkyl group and a tricyclo structure having many cyclic structures, and the like. The alkyl group (for example, the alkyl group of alkoxy groups and alkylthio groups) in the substituents to be described below also represents such a concept of an alkyl group. Specifically, preferred examples of the alkyl group include an alkyl group having 1 to 30 carbon atoms, for example, a methyl group, an ethyl group, an n-propyl group, an i-propyl group, a t-butyl group, an n-octyl group, an eicosyl group, a 2-chloroethyl group, a 2-cyanoethyl group, a 2-ethylhexyl group, and the like, preferred examples of the cycloalkyl group include a substituted or unsubstituted cycloalkyl group having 3 to 30 carbon atoms, for example, a cyclohexyl group, a cyclopentyl group, a 4-n-dodecylcyclohexyl group, and the like, and preferred examples of the bicycloalkyl group include a substituted or unsubstituted bicycloalkyl group having 5 to 30 carbon atoms, that is, a monovalent group in which one hydrogen atom is removed from bicycloalkane having 5 to 30 carbon atoms, for example, a bicyclo[1,2,2]heptan-2-yl group, a bicyclo[2,2,2]octan-3-yl group, and the like.

Preferred examples of the aralkyl group include a substituted or unsubstituted aralkyl group, and preferred examples of the substituted or unsubstituted aralkyl group include an aralkyl group having 7 to 30 carbon atoms. Examples thereof include a benzyl group and a 2-phenethyl group.

Examples of the alkenyl group include a straight, branched or cyclic, substituted or unsubstituted alkenyl group, including a cycloalkenyl group and a bicycloalkenyl group. Specifically, preferred examples of the alkenyl group include a substituted or unsubstituted alkenyl group having 2 to 30 carbon atoms, for example, a vinyl group, an allyl group, a prenyl group, a geranyl group, an oleyl group, and the like, preferred examples of the cycloalkenyl group include a substituted or unsubstituted cycloalkenyl group having 3 to 30 carbon atoms, that is, a monovalent group in which one hydrogen atom of cycloalkene having 3 to 30 carbon atoms is removed, for example, a 2-cyclopentene-1-yl group, a 2-cyclohexene-1-yl group, and the like, and examples of the bicycloalkenyl group include a substituted or unsubstituted bicycloalkenyl group, preferably, a substituted or unsubstituted bicycloalkenyl group having 5 to 30 carbon atoms, that is, a monovalent group in which one hydrogen atom of bicycloalkene having one double bond is removed, for example, a bicyclo[2,2,1]hept-2-en-1-yl group, a bicyclo[2,2,2]oct-2-en-4-yl group, and the like.

Preferred examples of the alkynyl group include a substituted or unsubstituted alkynyl group having 2 to 30 carbon atoms, for example, an ethynyl group, a propargyl group, a trimethylsilylethynyl group, and the like.

Preferred examples of the aryl group include a substituted or unsubstituted aryl group having 6 to 30 carbon atoms, for example, a phenyl group, a p-tolyl group, a naphthyl group, a m-chlorophenyl group, an o-hexadecanoylaminophenyl group, and the like.

Preferred examples of the heterocyclic group include a monovalent group in which one hydrogen atom is removed from a 5- or 6-membered substituted or unsubstituted aromatic or non-aromatic heterocyclic compound, and more preferred examples thereof include a 5- or 6-membered aromatic heterocyclic group having 3 to 30 carbon atoms, for example, a 2-furyl group, a 2-thienyl group, a 2-pyrimidinyl group, a 2-benzothiazolyl group, and the like.

Preferred examples of the alkoxy group include a substituted or unsubstituted alkoxy group having 1 to 30 carbon atoms, for example, a methoxy group, an ethoxy group, an isopropoxy group, a t-butoxy group, an n-octyloxy group, a 2-methoxyethoxy group and the like.

Preferred examples of the aryloxy group include a substituted or unsubstituted aryloxy group having 6 to 30 carbon atoms, for example, a phenoxy group, a 2-methylphenoxy group, a 4-t-butylphenoxy group, a 3-nitrophenoxy group, a 2-tetradecanoylaminophenoxy group and the like.

Preferred examples of the silyloxy group include a substituted or unsubstituted silyloxy group having 0 to 20 carbon atoms, for example, a trimethylsilyloxy group, a diphenylmethylsilyloxy group and the like.

Preferred examples of the heterocyclic oxy group include a substituted or unsubstituted heterocyclic oxy group having 2 to 30 carbon atoms, for example, a 1-phenyltetrazole-5-oxy group, a 2-tetrahydropyranyloxy group and the like.

Preferred examples of the acyloxy group include a formyloxy group, a substituted or unsubstituted alkylcarbonyloxy group having 2 to 30 carbon atoms, and a substituted or unsubstituted arylcarbonyloxy group having 6 to 30 carbon atoms, for example, an acetyloxy group, a pyvaloyloxy group, a stearoyloxy group, a benzoyloxy group, p-methoxyphenylcarbonyloxy group and the like.

Preferred examples of the carbamoyloxy group include a substituted or unsubstituted carbamoyloxy group having 1 to 30 carbon atoms, for example, a N,N-dimethylcarbamoyloxy group, a N,N-diethylcarbamoyloxy group, a morpholinocarbonyloxy group, a N,N-di-n-octylaminocarbonyloxy group, a N-n-octylcarbamoyloxy group and the like.

Preferred examples of the alkoxycarbonyloxy group include a substituted or unsubstituted alkoxycarbonyloxy group having 2 to 30 carbon atoms, for example, a methoxycarbonyloxy group, an ethoxycarbonyloxy group, a t-butoxycarbonyloxy group, an n-octylcarbonyloxy group and the like.

Preferred examples of the aryloxycarbonyloxy group include a substituted or unsubstituted aryloxycarbonyloxy group having 7 to 30 carbon atoms, for example, a phenoxycarbonyloxy group, a p-methoxyphenoxycarbonyloxy group, a p-n-hexadecyloxyphenoxycarbonyloxy group and the like.

Examples of the amino group include an alkylamino group, an arylamino group, a heterocyclicamino group, and preferred examples thereof include an amino group, a substituted or unsubstituted alkylamino group having 1 to 30 carbon atoms, and a substituted or substituted anylino group having 6 to 30 carbon atoms, for example, a methylamino group, a dimethylamino group, an anylino group, an N-methyl-anilino group, a diphenylamino group, a triazinylamino group and the like.

Preferred examples of the acylamino group include a formylamino group, a substituted or unsubstituted alkylcarbonylamino group having 1 to 30 carbon atoms, and a substituted or unsubstituted arylcarbonylamino group having 6 to 30 carbon atoms, for example, an acetylamino group, a pyvaloylamino group, a lauroylamino group, a benzoylamino group, a 3,4,5-tri-n-octyloxyphenylcarbonylamino group and the like.

Preferred examples of the aminocarbonylamino group include a substituted or unsubstituted aminocarbonylamino group having 1 to 30 carbon atoms, for example, a carbamoylamino group, an N,N-dimethylaminocarbonylamino group, an N,N-diethylaminocarbonylamino group, a morpholinocarbonylamino group and the like.

Preferred examples of the alkoxycarbonylamino group include a substituted or =substituted alkoxycarbonylamino group having 2 to 30 carbon atoms, for example, a methoxycarbonylamino group, an ethoxycarbonylamino group, a t-butoxycarbonylamino group, an n-octadecyloxycarbonylamino group, an N-methyl-methoxycarbonylamino group and the like.

Preferred examples of the aryloxycarbonylamino group include a substituted or unsubstituted aryloxycarbonylamino group having 7 to 30 carbon atoms, for example, a phenoxycarbonylamino group, a p-chlorophenoxycarbonylamino group, an m-n-octyloxyphenoxycarbonylamino group and the like.

Preferred examples of the sulfamoylamino group include a substituted or unsubstituted sulfamoylamino group having 0 to 30 carbon atoms, for example, a sulfamoylamino group, an N,N-dimethylaminosulfonylamino group, an N-n-octylaminosulfonylamino group and the like.

Preferred examples of the alkyl or arylsulfonylamino group include a substituted or unsubstituted alkylsulfonylamino group having 1 to 30 carbon atoms, and a substituted or unsubstituted arylsulfonylamino group having 6 to 30 carbon atoms, for example, a methylsulfonylamino group, a butylsulfonylamino group, a phenylsulfonylamino group, a 2,3,5-trichlorophenylsulfonylamino group, a p-methylphenylsulfonylamino group and the like. Preferred examples of the alkylthio group include a substituted or unsubstituted alkylthio group having 1 to 30 carbon atoms, for example, a methylthio group, an ethylthio group, an n-hexadecylthio group and the like.

Preferred examples of the arylthio group include a substituted or unsubstituted arylthio group having 6 to 30 carbon atoms, for example, a phenylthio group, a p-chlorophenylthio group, an m-methoxyphenylthio group and the like.

Preferred examples of the heterocyclic thio group include a substituted or unsubstituted heterocyclic thio group having 2 to 30 carbon atoms, for example, a 2-benzothiazolylthio group, a 1-phenyltetrazol-5-ylthio group and the like.

Preferred examples of the sulfamoyl group include a substituted or unsubstituted sulfamoyl group having 0 to 30 carbon atoms, for example, an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N'-phenylcarbamoyl) sulfamoyl group and the like.

Preferred examples of the alkyl or arylsulfinyl group include a substituted or unsubstituted alkylsulfinyl group having 1 to 30 carbon atoms, and a substituted or unsubstituted arylsulfinyl group having 6 to 30 carbon atoms, for example, a methylsulfinyl group, an ethylsulfinyl group, a phenylsulfinyl group, a p-methylphenylsulfinyl group and the like.

Preferred examples of the alkyl or arylsulfonyl group include a substituted or unsubstituted alkylsulfonyl group having 1 to 30 carbon atoms, and a substituted or unsubstituted arylsulfonyl group having 6 to 30 carbon atoms, for example, a methylsulfonyl group, an ethylsulfonyl group, a phenylsulfonyl group, a p-methylphenylsulfonyl group and the like.

Preferred examples of the acyl group include a formyl group, a substituted or unsubstituted alkylcarbonyl group having 2 to 30 carbon atoms, a substituted or unsubstituted arylcarbonyl group having 7 to 30 carbon atoms, and a substituted or unsubstituted heterocycliccarbonyl group having 2 to 30 carbon atoms, in which a carbon atom and a carbonyl group are bonded, for example, an acetyl group, a pyvaloyl group, a 2-chloroacetyl group, a stearoyl group, a benzoyl group, a p-n-octyloxyphenylcarbonyl group, a 2-pyridylcarbonyl group, a 2-furylcarbonyl group and the like.

Preferred examples of the aryloxycarbonyl group include a substituted or unsubstituted aryloxycarbonyl group having 7 to 30 carbon atoms, for example, a phenoxycarbonyl group, an o-chlorophenoxycarbonyl group, an m-nitrophenoxycarbonyl group, a p-t-butylphenoxycarbonyl group and the like.

Preferred examples of the alkoxycarbonyl group include a substituted or unsubstituted alkoxycarbonyl group having 2 to 30 carbon atoms, for example, a methoxycarbonyl group, an ethoxycarbonyl group, a t-butoxycarbonyl group, an n-octadecyloxycarbonyl group and the like.

Preferred examples of the carbamoyl group include a substituted or unsubstituted carbamoyl group having 1 to 30 carbon atoms, for example, a carbamoyl group, an N-methylcarbamoyl group, an N,N-dimethylcarbamoyl group, an N,N-di-n-octylcarbamoyl group, an N-(methylsulfonyl)carbamoyl group and the like.

Preferred examples of the aryl or heterocyclic azo group include a substituted or unsubstituted arylazo group having 6 to 30 carbon atoms, and a substituted or unsubstituted heterocyclicazo group having 3 to 30 carbon atoms, for example, phenylazo, p-chlorophenylazo, 5-ethyl thio-1,3,4-thiadiazol-2-ylazo and the like.

Preferred examples of the imide group include an N-succinimide group, an N-phthalimide group and the like.

Preferred examples of the phosphino group include a substituted or unsubstituted phosphino group having 0 to 30 carbon atoms, for example, a dimethylphosphino group, a diphenylphosphino group, a methylphenoxyphosphino group and the like.

Preferred examples of the phosphinyl group include a substituted or unsubstituted phosphinyl group having 0 to 30 carbon atoms, for example, a phosphinyl group, a dioctyloxyphosphinyl group, a diethoxyphosphinyl group and the like.

Preferred examples of the phosphinyloxy group include a substituted or unsubstituted phosphinyloxy group having 0 to 30 carbon atoms, for example, a diphenoxyphosphinyloxy group, a dioctyloxyphosphinyloxy group and the like.

Preferred examples of the phosphinylamino group include a substituted or unsubstituted phosphinylamino group having 0 to 30 carbon atoms, for example, a dimethoxyphosphinylamino group, a dimethylaminophosphinylamino group and the like.

Preferred examples of the silyl group include a substituted or unsubstituted silyl group having 0 to 30 carbon atoms, for example, a trimethylsilyl group, a t-butyldimethylsilyl group, a phenyldimethylsilyl group and the like.

(Ionic Hydrophilic Group)

Examples of an ionic hydrophilic group include a sulfo group, a carboxyl group, a thiocarboxyl group, a sulfino group, a phosphono group, a dihydroxyphosphino group, a quaternary ammonium group and the like. The ionic hydrophilic group is particularly preferably a sulfo group or a carboxyl group. In addition, the carboxyl group, the phosphono group and the sun group may be in a salt state, and examples of a counter cation which forms a salt include an ammonium ion, an alkali metal ion (for example, a lithium ion, a sodium ion and a potassium ion) and an organic cation (for example, a tetramethylammonium ion, a tetramethylguanidium ion and tetramethylphosphonium), and the counter cation is preferably a lithium salt, a sodium salt, a potassium salt or an ammonium salt, more preferably a lithium salt or a mixture salt containing a lithium salt as a main component, and most preferably a lithium salt.

Furthermore, in the present invention, when the compound is a salt, the salt is dissociated into ions, and is present in ink, but for convenience, the expression "contains a salt" is used.

Hereinafter, the compound represented by Formula (1) of the present invention will be described in detail.

[Compound Represented by Formula (I)]

The compound (colorant) represented by Formula (1) of the present invention includes a compound and a salt thereof, and a hydrate thereof.

Since introduced is a triazine unit having a specific linking group including a sulfamoyl group, in which C. I. Acid Red 289 having relatively high color development and high fastness is used as a mother body, even among xanthene compounds, the compound of the present invention exhibits effects that the colorant is prevented from being oxidatively decomposed by the sulfamoyl group of the linking group and becomes a highly color-developing dye having particularly excellent image fastness such as ozone resistance and light fastness, and the transfer of a colorant is suppressed by formation of intermolecular hydrogen bonds between colorants by the introduced triazine unit, and accordingly, moisture resistance (color migration depending on humidity) is also excellent.

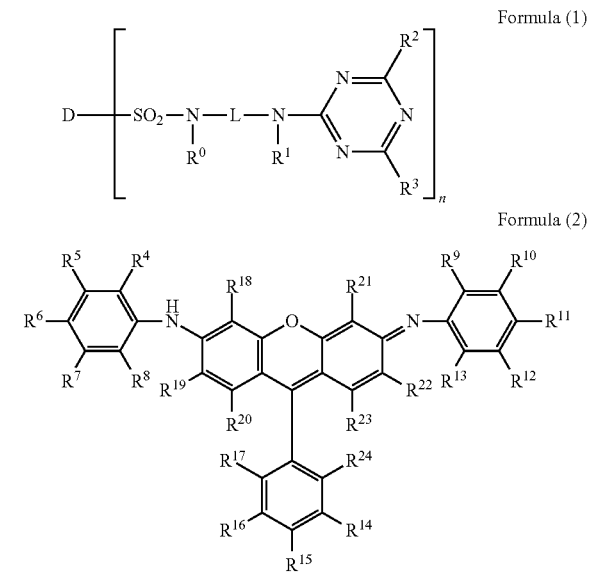

In Formula (1), $R^0$ to $R^3$ each independently represent a hydrogen atom or a substituent. $R^0$ and $R^1$, $R^0$ and L, or $R^1$ and L may be combined with each other to form a ring.

L represents a single bond or a divalent linking group.

D represents a residue in which n hydrogen atoms are removed from a compound represented by Formula (2).

n represents an integer of 1 or more. However, when a represents an integer of 2 or more, a plurality of $R^0$'s to $R^3$'s and L's may be the same or different.

In Formula (2), $R^4$ to $R^{24}$ each independently represent a hydrogen atom or a substituent.

However, the compound represented by Formula (1) has at least one ionic hydrophilic group.

In Formula (1), $R^0$ to $R^3$ each independently represent a hydrogen atom or a substituent. Examples of the substituent include Group A of substituents as described above.

$R^0$ and $R^1$ each independently represent a hydrogen atom or a substituent, and are preferably a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heterocyclic group and a substituted or unsubstituted alkenyl group, more preferably a hydrogen atom and a substituted or unsubstituted alkyl group, and most preferably a hydrogen atom.

$R^2$ and $R^3$ each independently represent a hydrogen atom or a substituent, and are preferably a hydrogen atom or Group A of substituents, preferably a hydrogen atom, a substituted or unsubstituted amino group, a hydroxyl group, a substituted or unsubstituted alkoxy group, a substituted or unsubstituted aryloxy group, a substituted or unsubstituted alkylthio group, a substituted or unsubstituted arylthio group and a substituted or unsubstituted heterocyclic thio group, and more preferably a substituted or unsubstituted amino group.

When the substituent represented by $R^2$ and $R^3$ further includes a substituent, examples of the substituent include Group A of substituents, and an alkyl group, an aryl group or a heterocyclic group is preferred. These substituents may be substituted by Group A of substituents, and are more preferably substituted by an ionic hydrophilic group.

At least one of $R^0$ to $R^3$ is preferably a group having a sulfonic acid group, a carboxyl group or an ionic hydrophilic group as a substituent. Examples of the ionic hydrophilic group include a sulfo group, a carboxyl group, a phosphono group, a quaternary ammonium group, and the like. The ionic hydrophilic group is preferably a carboxyl group, a phosphono group and a sulfo group, and particularly preferably a carboxyl group and a sulfo group. The carboxyl group, the phosphono group and the sulfo group may be in a salt state, and examples of the counter ion which forms a salt include an ammonium ion, an alkali metal ion (for example, a lithium ion, a sodium ion and a potassium ion) and an organic cation (for example, a tetramethylammonium ion, a tetramethylguanidium ion and tetramethylphosphonium). Among the counter ions, an alkali metal salt is preferred, and particularly, a lithium ion is particularly preferred because the ion increases solubility of a compound and enhances ink stability. The number of ionic hydrophilic groups is preferably at least two in one molecule of the compound represented by Formula (1), and preferably at least two to eight ionic hydrophilic groups selected particularly from the sulfo group and the carboxyl group, and particularly preferably two to four.

$R^0$ and $R^1$, $R^0$ and L, or $R^1$ and L may be combined with each other to form a ring. A ring, which $R^0$ and $R^1$, and L, or $R^1$ and L are combined with each other to form, is preferably a 5- to 10-membered ring, and more preferably a 5- or 6-membered ring. When $R^0$ and $R^1$, $R^0$ and L, or $R^1$ and L are combined with each other to form a ring, $R^0$ and $R^1$ are preferably an alkylene group. The ring to be formed may have a substituent, and examples of the substituent include Group A of substituents, and an alkyl group is preferred.

Furthermore, when $R^0$ and $R^1$, or $R^1$ and L are combined with each other to form a ring, L becomes a trivalent linking group, and examples of the trivalent linking group include a trivalent linking group obtained by removing any one hydrogen atom from a divalent linking group as L to be described below.

In Formula (1), L represents a single bond or a divalent linking group. Examples of the divalent linking group include an oxy group (—O—), a thio group (—S—), a carbonyl group (—CO—), a sulfonyl group (—SO$_2$—), an imine group (—NH—), an alkylene group (preferably an alkylene group having 1 to 10 carbon atoms, and more preferably an alkylene group having 2 to 6 carbon atoms), an arylene group (preferably an arylene group having 6 to 20 carbon atoms, and more preferably an arylene group having 6 to 10 carbon atoms), a cycloalkylene group (preferably a cycloalkylene group having 3 to 15 carbon atoms, and more preferably a cycloalkylene group having 5 to 10 carbon atoms), and a group formed by combining these groups. These groups may have a substituent, and examples of the substituent include Group A of substituents, and an alkyl group is preferred.

L is preferably an alkylene group having 1 to 10 carbon atoms, which may have a substituent and an arylene group having 6 to 10 carbon atoms, which may have a substituent, more preferably an alkylene group having 1 to 10 carbon atoms, which may have a substituent, and still more preferably an alkylene group having 2 to 6 carbon atoms, which may have a substituent.

Hereinafter, specific examples of a triazine unit represented in the parenthesis of Formula (1) will be described, but the present invention is not limited to these specific examples.

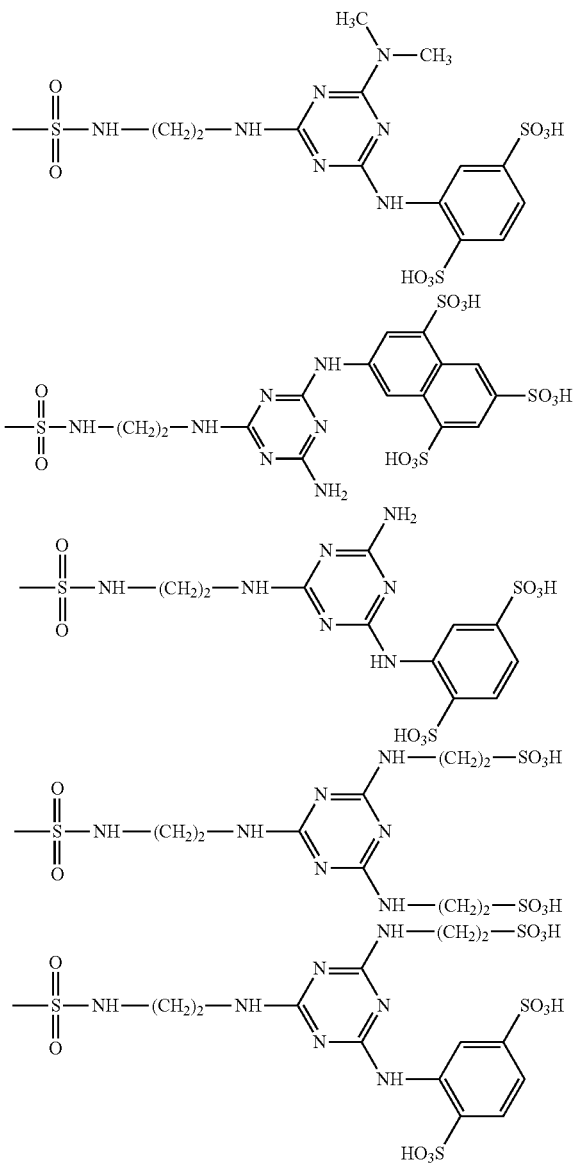
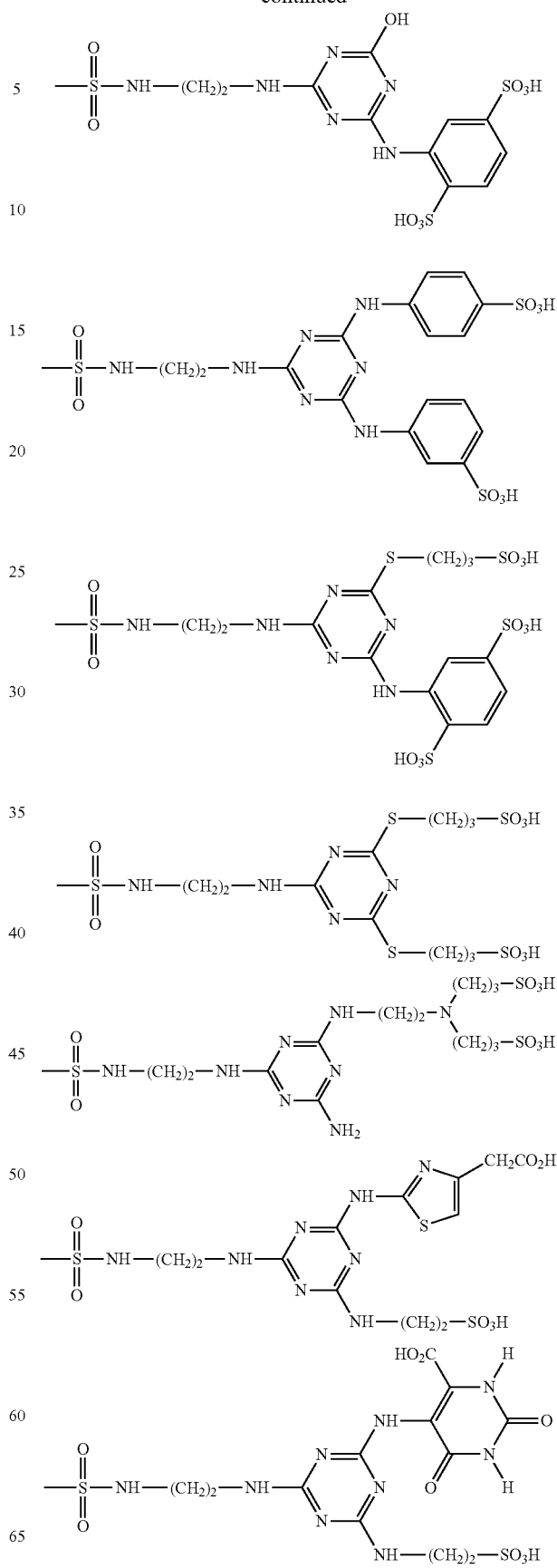

-continued
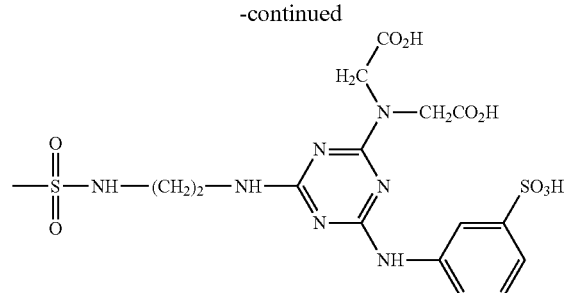
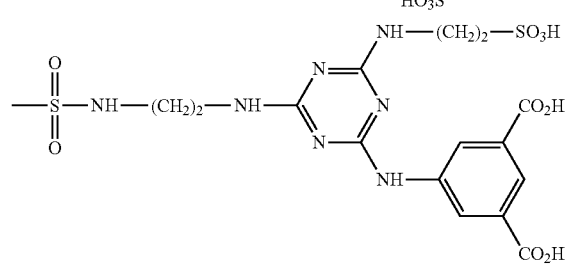
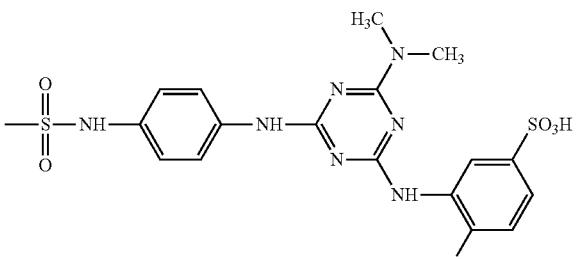
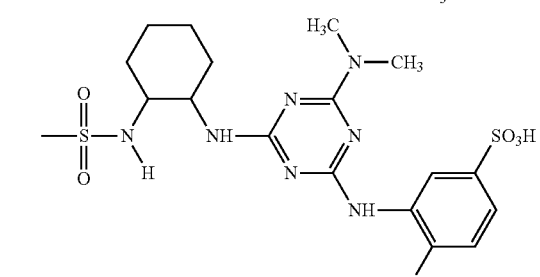
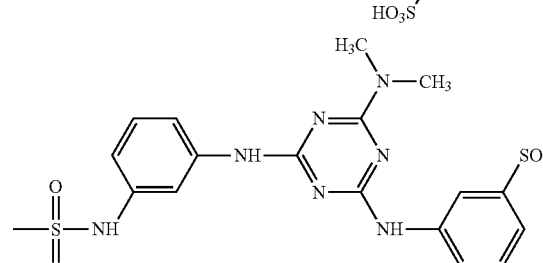
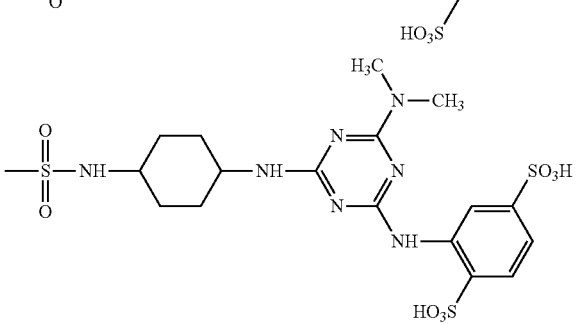
-continued
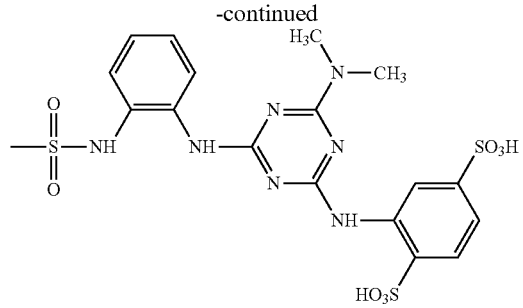
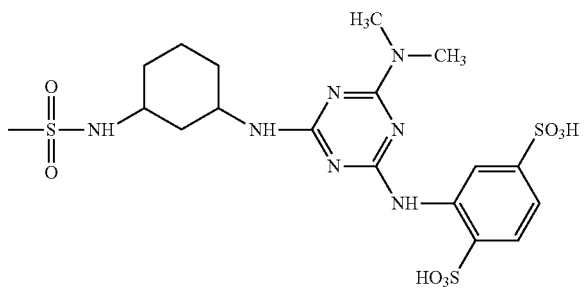
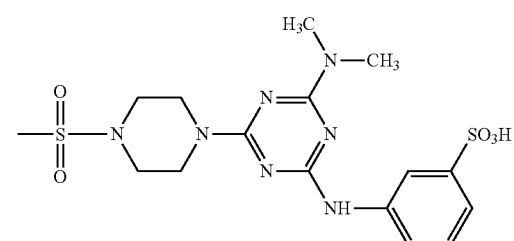
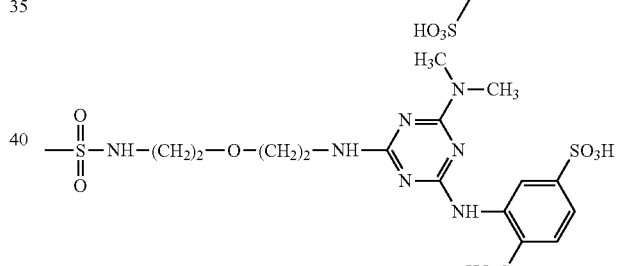
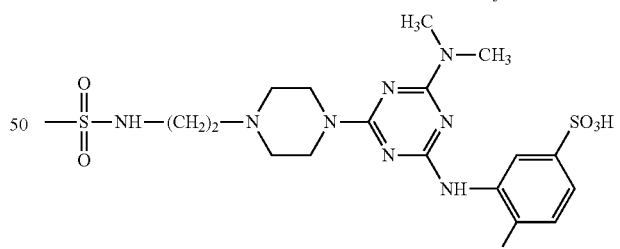
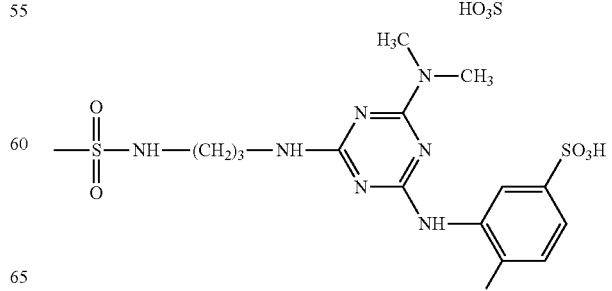

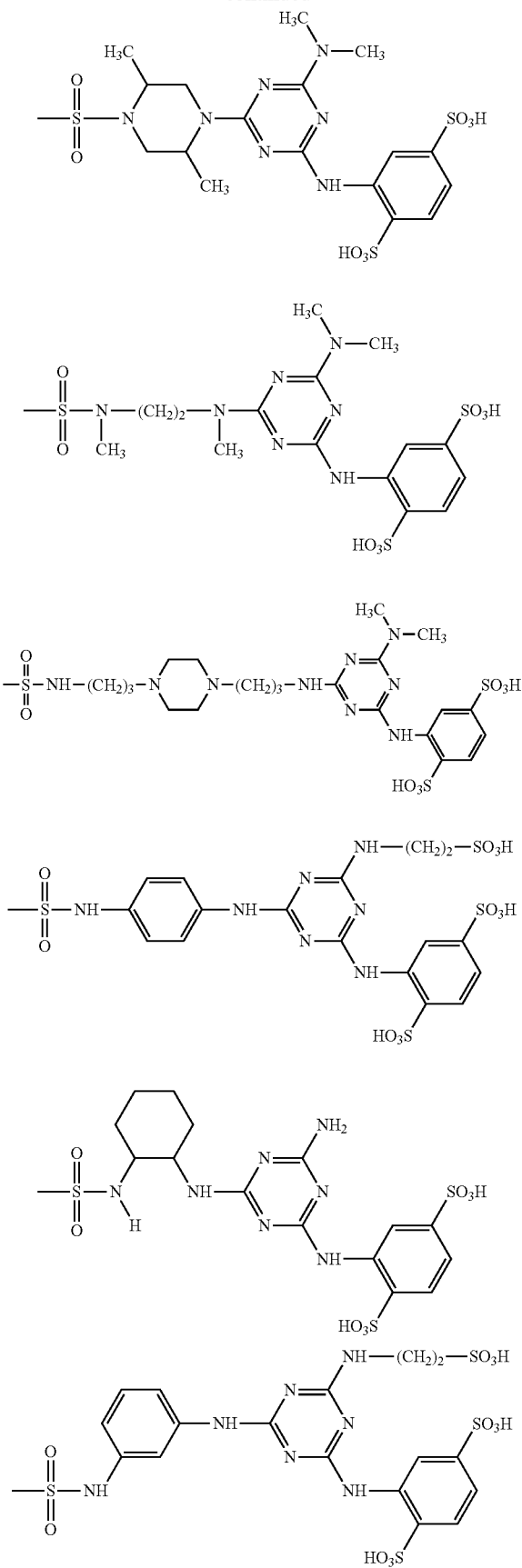
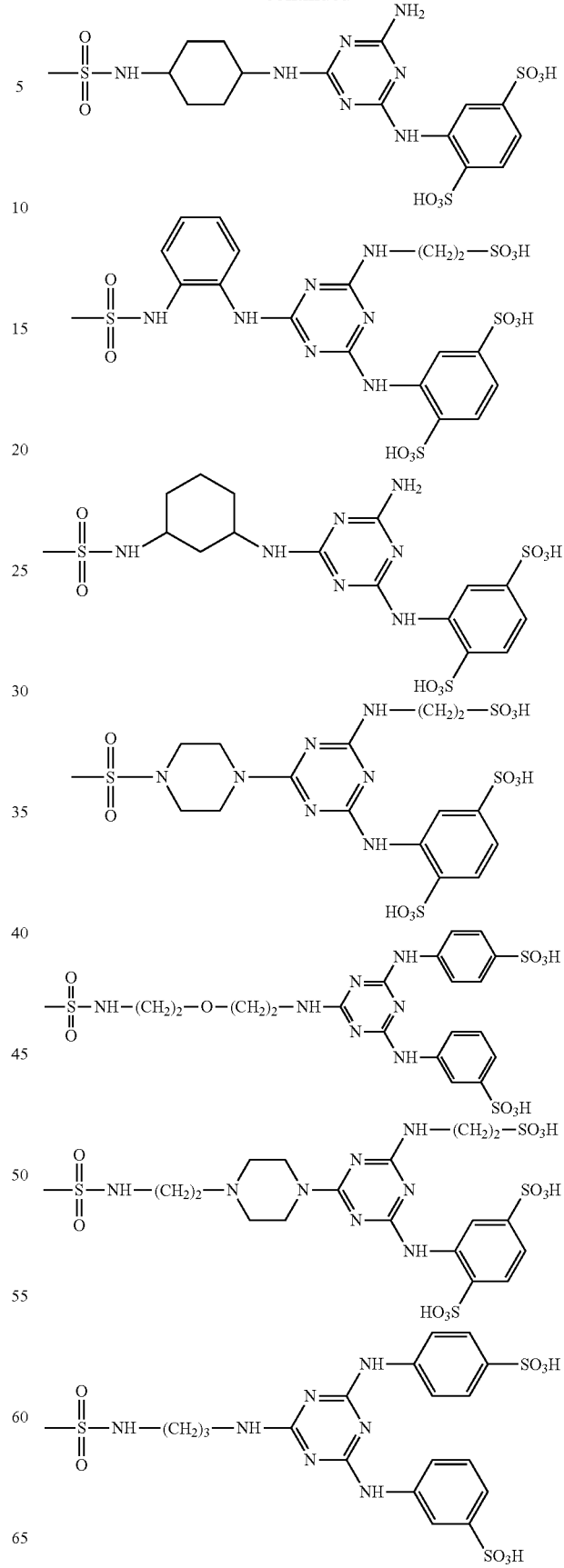

-continued

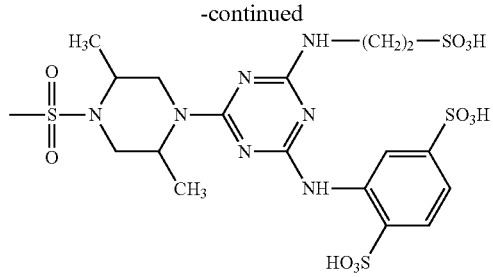

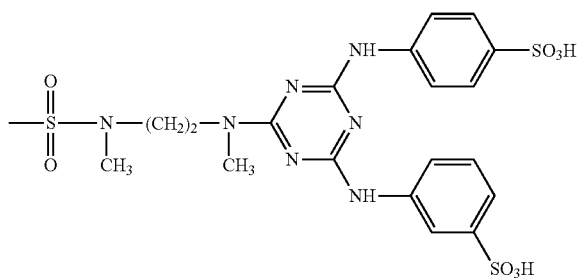

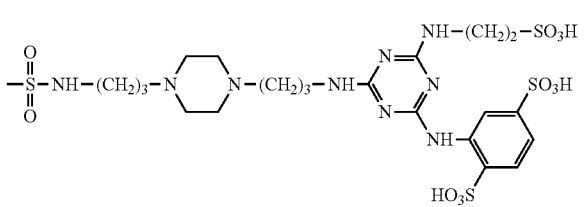

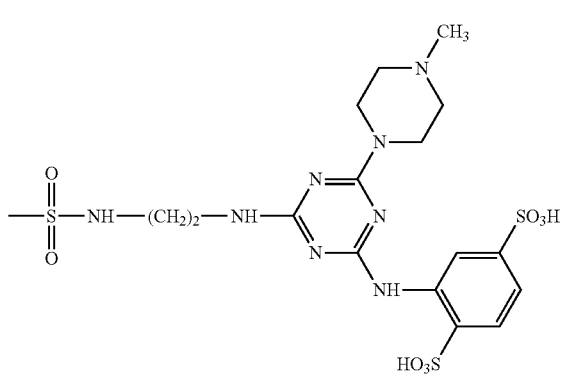

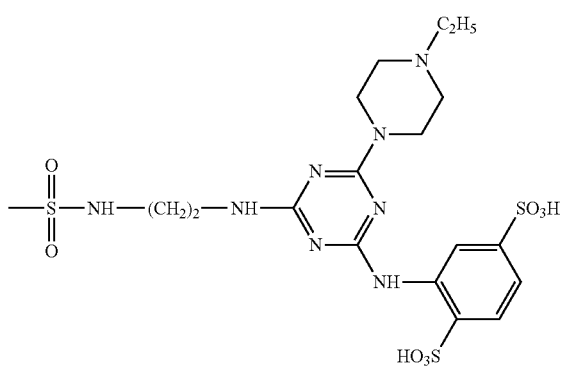

-continued

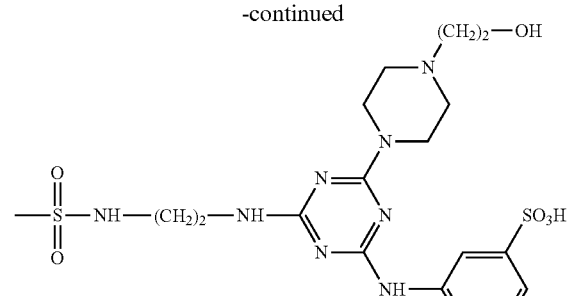

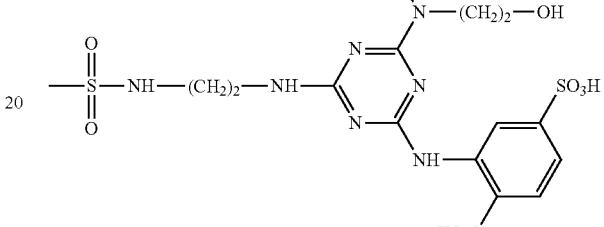

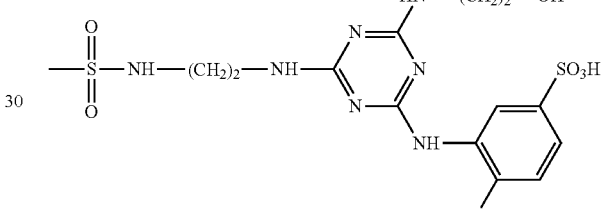

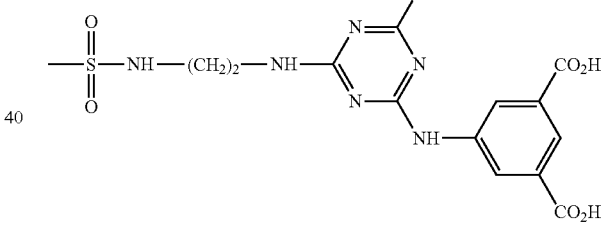

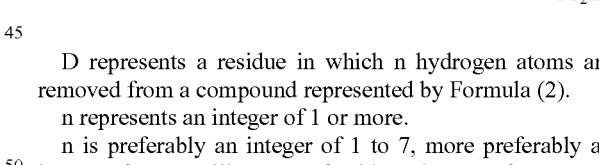

D represents a residue in which n hydrogen atoms are removed from a compound represented by Formula (2).

n represents an integer of 1 or more.

n is preferably an integer of 1 to 7, more preferably an integer of 1 to 4, still more preferably an integer of 1 to 3, and particularly preferably 1 or 2.

In Formula (2), $R^4$ to $R^{24}$ each independently represent a hydrogen atom or a substituent. Examples of the substituent include Group A of substituents as described above.

In Formula (2), it is preferred that $R^4$, $R^8$, $R^9$ and $R^{13}$ each independently represents hydrogen atom or an aliphatic group. The aliphatic group may be =substituted or have a substituent and may be saturated or unsaturated, and preferably an aliphatic group having 1 to 20 carbon atoms in total, more preferably an alkyl group having 1 to 20 carbon atoms in total, and still more preferably an alkyl group having 1 to 10 carbon atoms in total. Examples thereof include a methyl group, an ethyl group, a vinyl group, an allyl group, an ethynyl group, an isopropenyl group and a 2-ethylhexyl group. It is preferred that $R^4$, $R^8$, $R^9$ and $R^{13}$ each independently represent an aliphatic group from the viewpoint of hue.

It is preferred that in Formula (2), $R^5$ to $R^7$, $R^{10}$ to $R^{12}$ and $R^{14}$ to $R^{23}$ represent a hydrogen atom from the viewpoint of easiness of synthesis.

It is preferred that in Formula (2), $R^{24}$ represents a hydrogen atom or an ionic hydrophilic group. Further, it is preferred that in Formula (1), D represents a residue in which n hydrogen atoms are removed from hydrogen atoms as $R^5$ to $R^7$, $R^{10}$ to $R^{12}$ and $R^{24}$ of the compound represented by Formula (2) from the viewpoint of easiness of synthesis and hue. However, in this case, n represents an integer of 1 to 7. n is preferably an integer of 1 to 4, more preferably an integer of 1 to 3, and particularly preferably 1 or 2. When a is 1 or more, improvement effects are exhibited in moisture resistance, but when a is excessively high, n is preferably within the range because print concentration per unit weight is not sufficiently exhibited due to an increase in molecular weight. Further, it is preferred that D is a residue in which at least one hydrogen atom is removed from hydrogen atoms as $R^{10}$ to $R^{12}$ and $R^{24}$ of the compound represented by Formula (2). When $R^{24}$ is not a hydrogen atom for forming residue by removing a hydrogen atom from the compound represented by Formula (2), it is more preferred that $R^{24}$ is the ionic hydrophilic group.

Hereinafter, specific examples of the compound of the present invention, which is represented by Formula (1), will be described, but the present invention is not limited to these specific examples. a, b, and c in the Tables each mean a ratio of each substituent introduced as substituent R in the obtained compound of the present invention represented by Formula (1).

TABLE 1

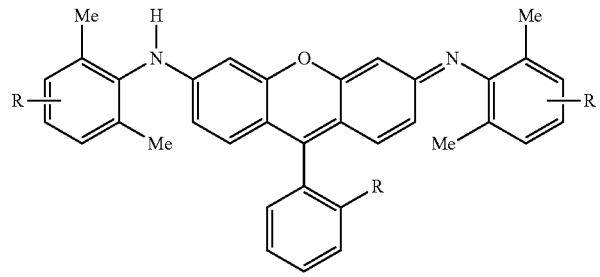

| Exemplarly Compound | R | |
|---|---|---|
| 1 | —(H)$_a$<br>—(SO$_3$H)$_b$<br>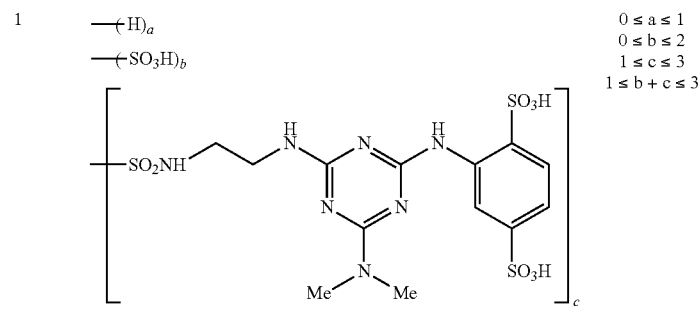 | $0 \leq a \leq 1$<br>$0 \leq b \leq 2$<br>$1 \leq c \leq 3$<br>$1 \leq b + c \leq 3$ |
| 2 | —(H)$_a$<br>—(SO$_3$H)$_b$<br>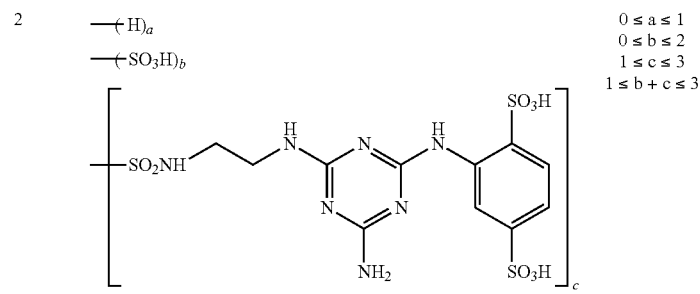 | $0 \leq a \leq 1$<br>$0 \leq b \leq 2$<br>$1 \leq c \leq 3$<br>$1 \leq b + c \leq 3$ |

TABLE 1-continued
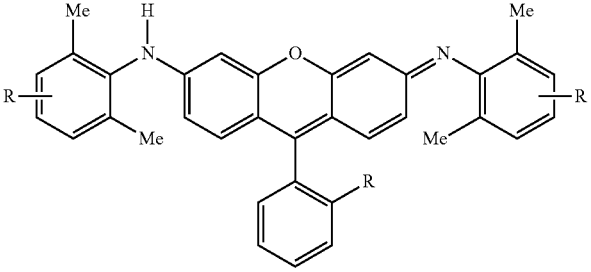
| Exemplarly Compound | R | |
|---|---|---|
| 3 | —(H)$_a$<br>—(SO$_3$H)$_b$<br>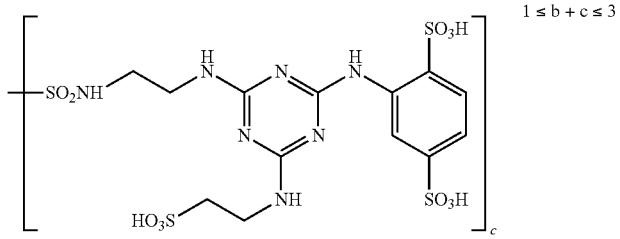 | $0 \leq a \leq 1$<br>$0 \leq b \leq 2$<br>$1 \leq c \leq 3$<br>$1 \leq b + c \leq 3$ |
| 4 | —(H)$_a$<br>—(SO$_3$H)$_b$<br>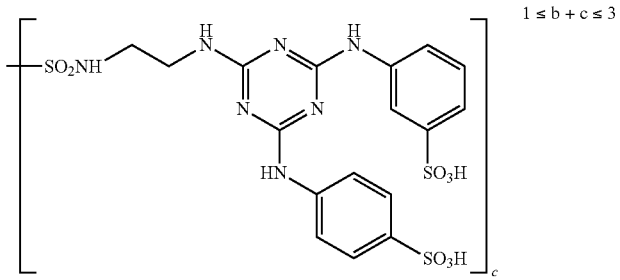 | $0 \leq a \leq 1$<br>$0 \leq b \leq 2$<br>$1 \leq c \leq 3$<br>$1 \leq b + c \leq 3$ |
| 5 | —(H)$_a$<br>—(SO$_3$H)$_b$<br>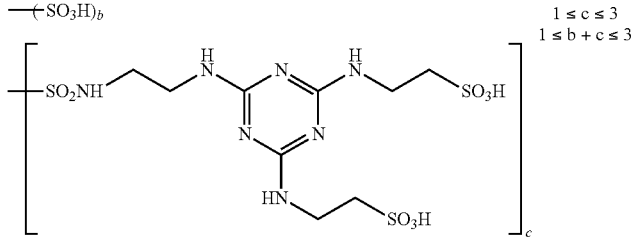 | $0 \leq a \leq 1$<br>$0 \leq b \leq 2$<br>$1 \leq c \leq 3$<br>$1 \leq b + c \leq 3$ |

TABLE 2

[Structure: xanthene-based dye with two N-(2,6-dimethylphenyl)amino groups bearing R substituents, and a phenyl group at the 9-position bearing R]

| Exemplarly Compound | R | |
|---|---|---|
| 6 | —(H)$_a$<br>—(SO$_3$H)$_b$<br>[—SO$_2$NH—CH$_2$CH$_2$—NH—(triazine with N(CH$_2$CH$_2$OH)$_2$ branch)—NH—(benzene with 2,5-di-SO$_3$H)]$_c$ | $0 \leq a \leq 1$<br>$0 \leq b \leq 2$<br>$1 \leq c \leq 3$<br>$1 \leq b + c \leq 3$ |
| 7 | —(H)$_a$<br>—(SO$_3$H)$_b$<br>[—SO$_2$NH—CH$_2$CH$_2$—NH—(triazine with NHCH$_2$CH$_2$OH branch)—NH—(benzene with 2,5-di-SO$_3$H)]$_c$ | $0 \leq a \leq 1$<br>$0 \leq b \leq 2$<br>$1 \leq c \leq 3$<br>$1 \leq b + c \leq 3$ |
| 8 | —(H)$_a$<br>—(SO$_3$H)$_b$<br>[—SO$_2$NH—CH$_2$CH$_2$—NH—(triazine with N-methylpiperazinyl branch)—NH—(benzene with 2,5-di-SO$_3$H)]$_c$ | $0 \leq a \leq 1$<br>$0 \leq b \leq 2$<br>$1 \leq c \leq 3$<br>$1 \leq b + c \leq 3$ |
| 9 | —(H)$_a$<br>—(SO$_3$H)$_b$<br>[—SO$_2$NH—CH$_2$CH$_2$—NH—(triazine with NH$_2$ branch)—NH—(benzene with 3,5-di-CO$_2$H)]$_c$ | $0 \leq a \leq 1$<br>$0 \leq b \leq 2$<br>$1 \leq c \leq 3$<br>$1 \leq b + c \leq 3$ |

TABLE 2-continued

[Structure: xanthene-based dye with two N-(2,6-dimethylphenyl)amino groups bearing R substituents, central xanthene oxygen, and a pendant phenyl group with R substituent]

| Exemplarly Compound | R | |
|---|---|---|
| 10 | —(H)$_a$<br>—(SO$_3$H)$_b$<br>—[SO$_2$NH—CH$_2$CH$_2$—NH—(triazine with S—CH$_2$CH$_2$CH$_2$—SO$_3$H and S—CH$_2$CH$_2$CH$_2$—SO$_3$H)]$_c$ | $0 \leq a \leq 1$<br>$0 \leq b \leq 2$<br>$1 \leq c \leq 3$<br>$1 \leq b + c \leq 3$ |

[Structure: similar xanthene-based dye framework]

| Exemplarly Compound | R | |
|---|---|---|
| 11 | —(H)$_a$<br>—(SO$_3$H)$_b$<br>—[SO$_2$—NH—(CH$_2$)$_2$—NH—(triazine with NH$_2$ and HN-naphthalene trisulfonic acid)]$_c$ | $0 \leq a \leq 1$<br>$0 \leq b \leq 2$<br>$1 \leq c \leq 3$<br>$1 \leq b + c \leq 3$ |
| 12 | —(H)$_a$<br>—(SO$_3$H)$_b$<br>—[SO$_2$—NH—(CH$_2$)$_3$—NH—(triazine with HN—(CH$_2$)$_2$—SO$_3$H and NH—(CH$_2$)$_2$—SO$_3$H)]$_c$ | $0 \leq a \leq 1$<br>$0 \leq b \leq 2$<br>$1 \leq c \leq 3$<br>$1 \leq b + c \leq 3$ |

-continued
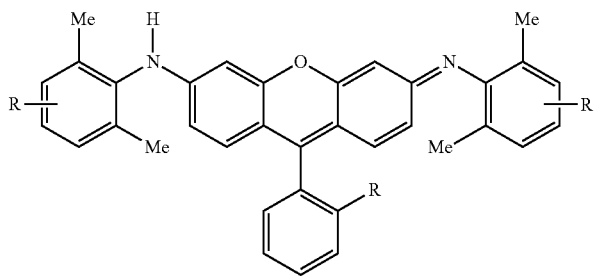
| Exemplarly Compound | R | |
|---|---|---|
| 13 | —(H)$_a$<br>—(SO$_3$H)$_b$<br>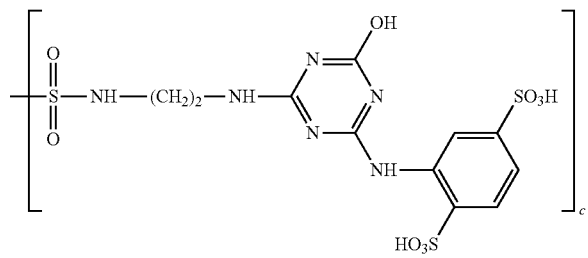 | $0 \le a \le 1$<br>$0 \le b \le 2$<br>$1 \le c \le 3$<br>$1 \le b + c \le 3$ |
| 14 | —(H)$_a$<br>—(SO$_3$H)$_b$<br>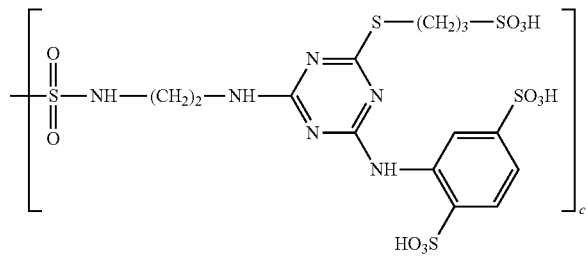 | $0 \le a \le 1$<br>$0 \le b \le 2$<br>$1 \le c \le 3$<br>$1 \le b + c \le 3$ |
| 15 | —(H)$_a$<br>—(SO$_3$H)$_b$<br>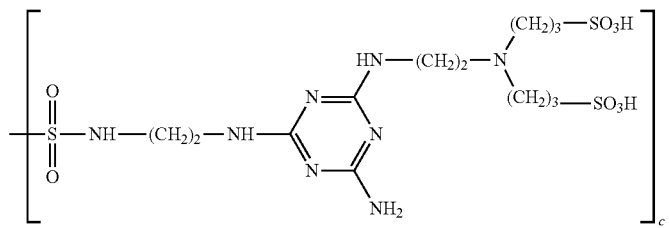 | $0 \le a \le 1$<br>$0 \le b \le 2$<br>$1 \le c \le 3$<br>$1 \le b + c \le 3$ |

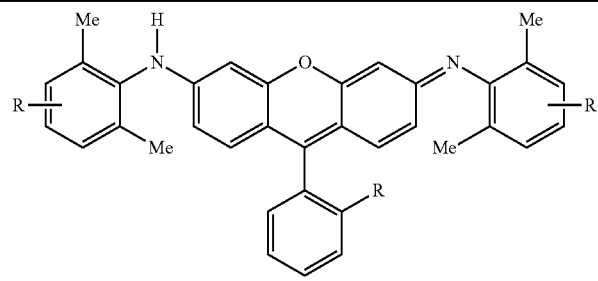
| Exemplarly Compound | R | |
|---|---|---|
| 16 | —(H)$_a$<br>—(SO$_3$H)$_b$<br>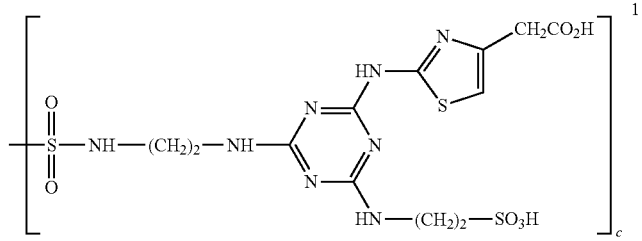 | $0 \leq a \leq 1$<br>$0 \leq b \leq 2$<br>$1 \leq c \leq 3$<br>$1 \leq b + c \leq 3$ |
| 17 | —(H)$_a$<br>—(SO$_3$H)$_b$<br>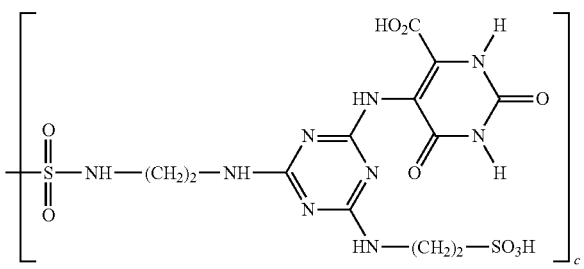 | $0 \leq a \leq 1$<br>$0 \leq b \leq 2$<br>$1 \leq c \leq 3$<br>$1 \leq b + c \leq 3$ |
| 18 | —(H)$_a$<br>—(SO$_3$H)$_b$<br>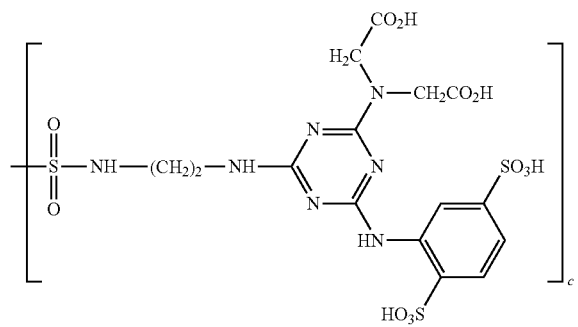 | $0 \leq a \leq 1$<br>$0 \leq b \leq 2$<br>$1 \leq c \leq 3$<br>$1 \leq b + c \leq 3$ |

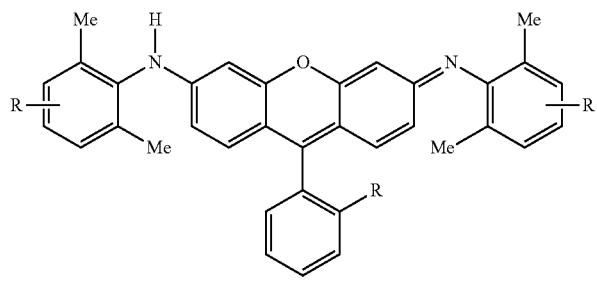
| Exemplarly Compound | R | |
|---|---|---|
| 19 | —(H)$_a$<br>—(SO$_3$H)$_b$<br>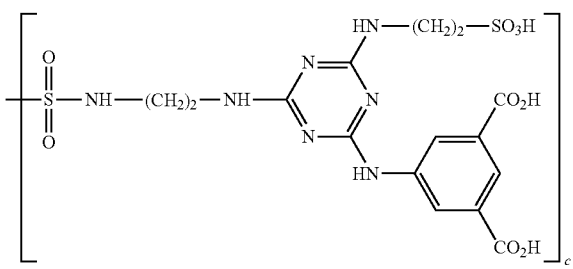 | $0 \leq a \leq 1$<br>$0 \leq b \leq 2$<br>$1 \leq c \leq 3$<br>$1 \leq b + c \leq 3$ |
| 20 | —(H)$_a$<br>—(SO$_3$H)$_b$<br>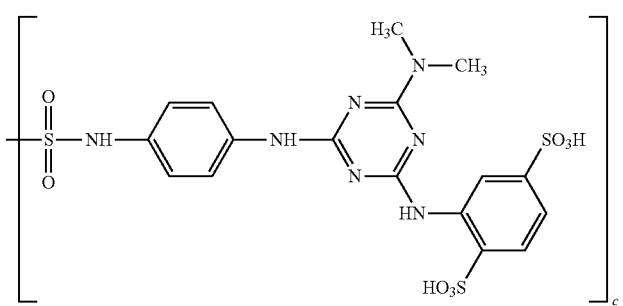 | $0 \leq a \leq 1$<br>$0 \leq b \leq 2$<br>$1 \leq c \leq 3$<br>$1 \leq b + c \leq 3$ |

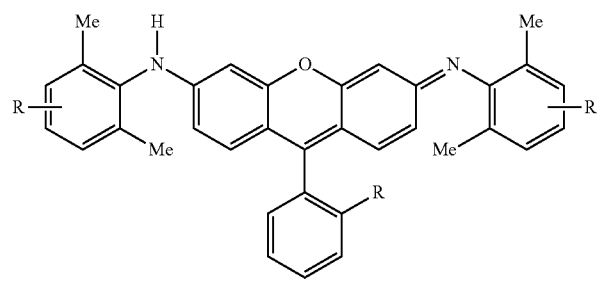
| Exemplarly Compound | R | |
|---|---|---|
| 21 | —(H)$_a$<br>—(SO$_3$H)$_b$<br>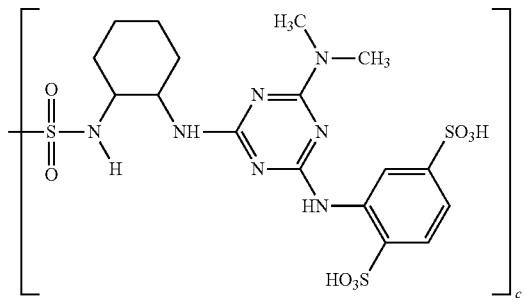 | $0 \leq a \leq 1$<br>$0 \leq b \leq 2$<br>$1 \leq c \leq 3$<br>$1 \leq b + c \leq 3$ |
| 22 | —(H)$_a$<br>—(SO$_3$H)$_b$<br>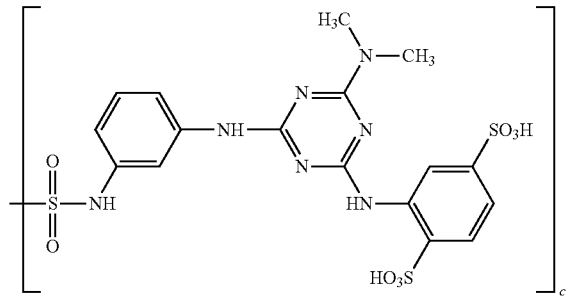 | $0 \leq a \leq 1$<br>$0 \leq b \leq 2$<br>$1 \leq c \leq 3$<br>$1 \leq b + c \leq 3$ |
| 23 | —(H)$_a$<br>—(SO$_3$H)$_b$<br>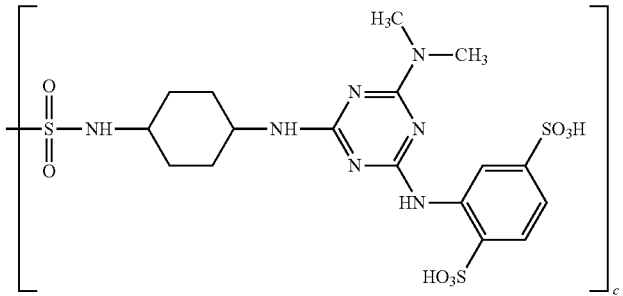 | $0 \leq a \leq 1$<br>$0 \leq b \leq 2$<br>$1 \leq c \leq 3$<br>$1 \leq b + c \leq 3$ |

-continued
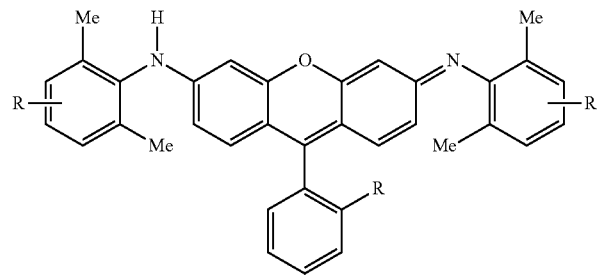
| Exemplarly Compound | R |
|---|---|
| 24 | —(H)$_a$  —(SO$_3$H)$_b$ 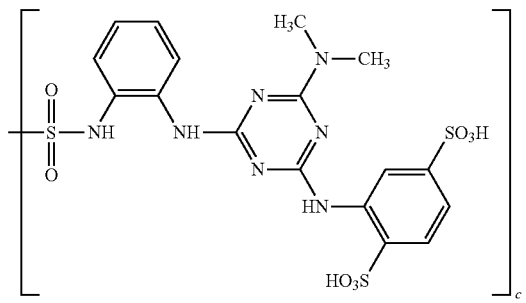 | $0 \leq a \leq 1$  $0 \leq b \leq 2$  $1 \leq c \leq 3$  $1 \leq b+c \leq 3$ |
|---|---|---|
| 25 | —(H)$_a$  —(SO$_3$H)$_b$ 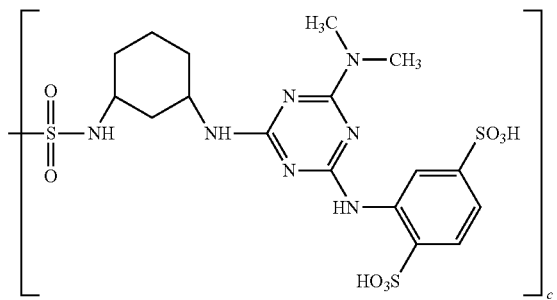 | $0 \leq a \leq 1$  $0 \leq b \leq 2$  $1 \leq c \leq 3$  $1 \leq b+c \leq 3$ |

TABLE 6
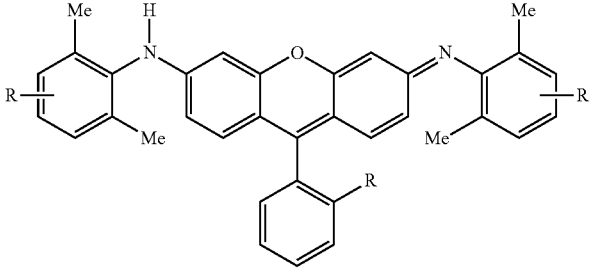
| Exemplarly Compound | R | |
|---|---|---|
| 26 | 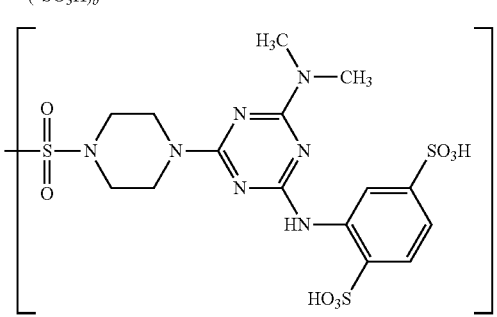 | 0 ≤ a ≤ 1<br>0 ≤ b ≤ 2<br>1 ≤ c ≤ 3<br>1 ≤ b + c ≤ 3 |
| 27 | 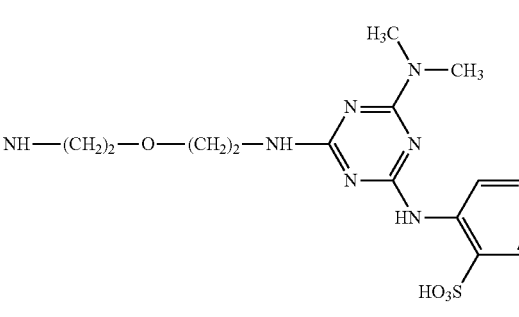 | 0 ≤ a ≤ 1<br>0 ≤ b ≤ 2<br>1 ≤ c ≤ 3<br>1 ≤ b + c ≤ 3 |
| 28 | 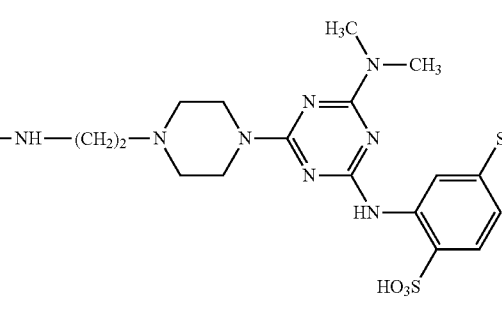 | 0 ≤ a ≤ 1<br>0 ≤ b ≤ 2<br>1 ≤ c ≤ 3<br>1 ≤ b + c ≤ 3 |

TABLE 6-continued
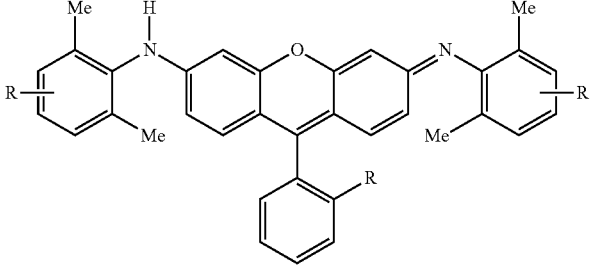
| Exemplarly Compound | R | |
|---|---|---|
| 29 | 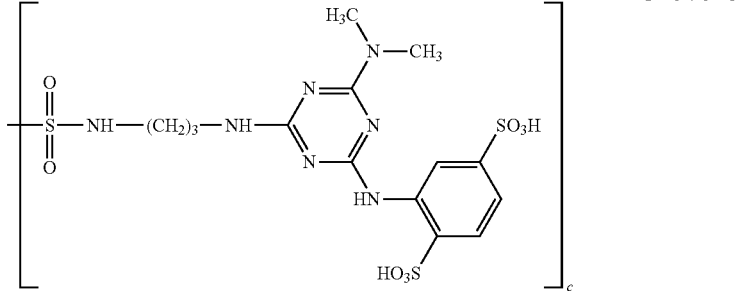 | $0 \leq a \leq 1$<br>$0 \leq b \leq 2$<br>$1 \leq c \leq 3$<br>$1 \leq b + c \leq 3$ |
| 30 | 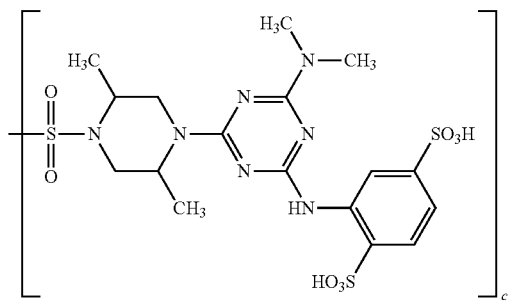 | $0 \leq a \leq 1$<br>$0 \leq b \leq 2$<br>$1 \leq c \leq 3$<br>$1 \leq b + c \leq 3$ |

TABLE 7
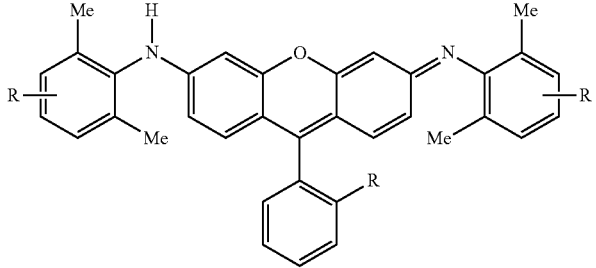
| Exemplarly Compound | R | |
|---|---|---|
| 31 | —(H)$_a$<br>—(SO$_3$H)$_b$<br>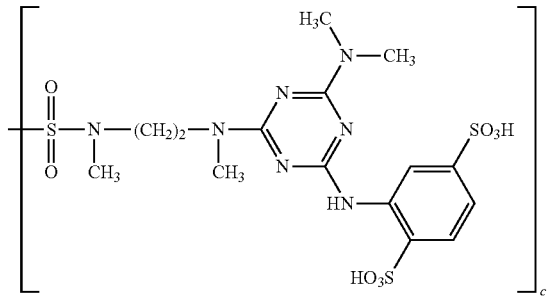 | $0 \le a \le 1$<br>$0 \le b \le 2$<br>$1 \le c \le 3$<br>$1 \le b + c \le 3$ |
| 32 | —(H)$_a$<br>—(SO$_3$H)$_b$<br>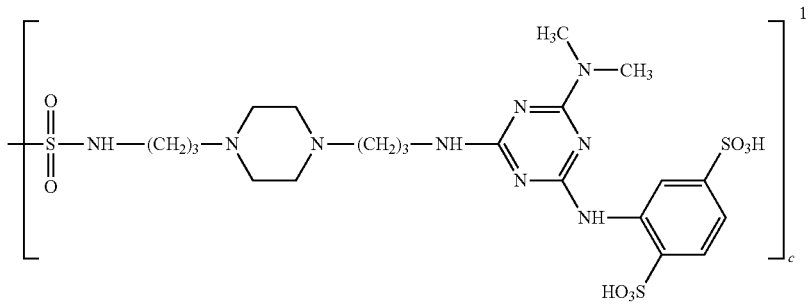 | $0 \le a \le 1$<br>$0 \le b \le 2$<br>$1 \le c \le 3$<br>$1 \le b + c \le 3$ |
| 33 | —(H)$_a$<br>—(SO$_3$H)$_b$<br>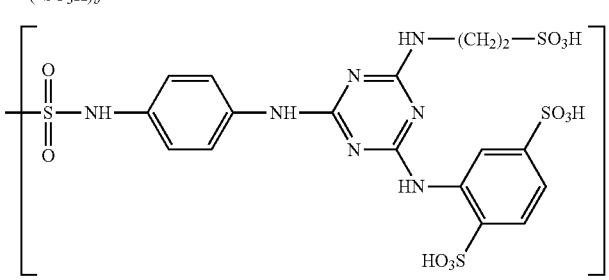 | $0 \le a \le 1$<br>$0 \le b \le 2$<br>$1 \le c \le 3$<br>$1 \le b + c \le 3$ |

TABLE 7-continued

[Structure: xanthene dye core with two 2,6-dimethylphenyl-amino/imino substituents bearing R groups, and a phenyl group with R substituent at the 9-position]

| Exemplarly Compound | R | |
|---|---|---|
| 34 | —(H)$_a$<br>—(SO$_3$H)$_b$<br>[Structure showing sulfonamide linked to cyclohexane-diamine, linked via NH to triazine bearing NH$_2$ and NH-phenyl(SO$_3$H)(SO$_3$H) group, with subscript c] | $0 \leq a \leq 1$<br>$0 \leq b \leq 2$<br>$1 \leq c \leq 3$<br>$1 \leq b + c \leq 3$ |
| 35 | —(H)$_a$<br>—(SO$_3$H)$_b$<br>[Structure showing sulfonamide linked to meta-phenylenediamine, linked via NH to triazine bearing NH—(CH$_2$)$_2$—SO$_3$H and NH-phenyl(SO$_3$H)(SO$_3$H) group, with subscript c] | $0 \leq a \leq 1$<br>$0 \leq b \leq 2$<br>$1 \leq c \leq 3$<br>$1 \leq b + c \leq 3$ |

TABLE 8
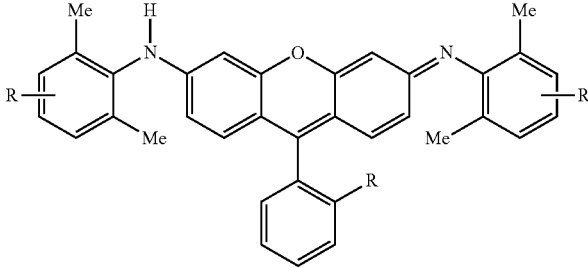
| Exemplarly Compound | R | |
|---|---|---|
| 36 | —(H)$_a$<br>—(SO$_3$H)$_b$<br>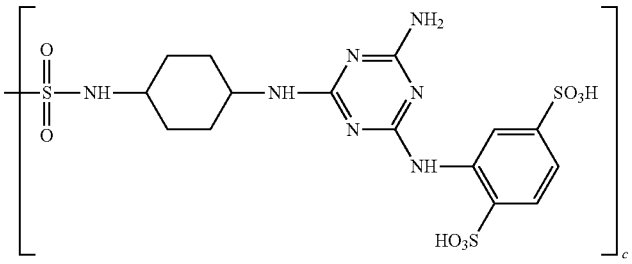 | 0 ≤ a ≤ 1<br>0 ≤ b ≤ 2<br>1 ≤ c ≤ 3<br>1 ≤ b + c ≤ 3 |
| 37 | —(H)$_a$<br>—(SO$_3$H)$_b$<br>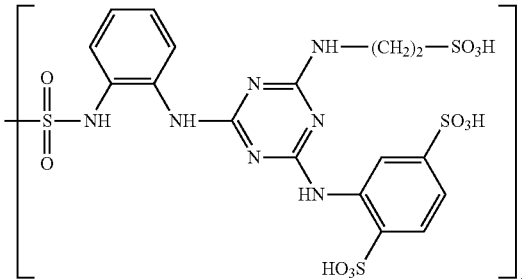 | 0 ≤ a ≤ 1<br>0 ≤ b ≤ 2<br>1 ≤ c ≤ 3<br>1 ≤ b + c ≤ 3 |
| 38 | —(H)$_a$<br>—(SO$_3$H)$_b$<br>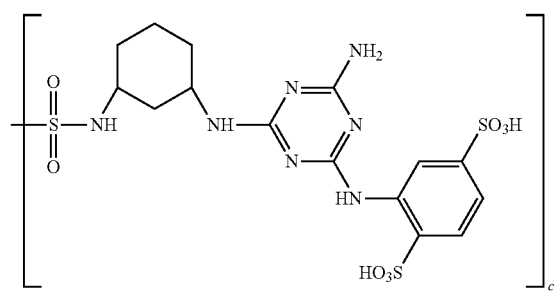 | 0 ≤ a ≤ 1<br>0 ≤ b ≤ 2<br>1 ≤ c ≤ 3<br>1 ≤ b + c ≤ 3 |

TABLE 8-continued
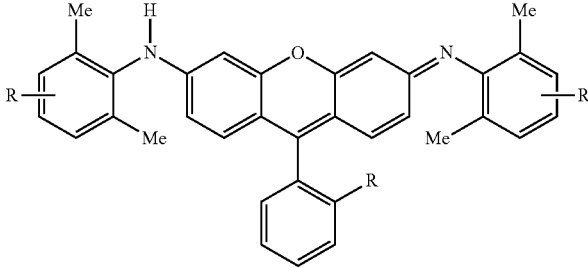
| Exemplarly Compound | R | |
|---|---|---|
| 39 | —(H)$_a$<br>—(SO$_3$H)$_b$<br>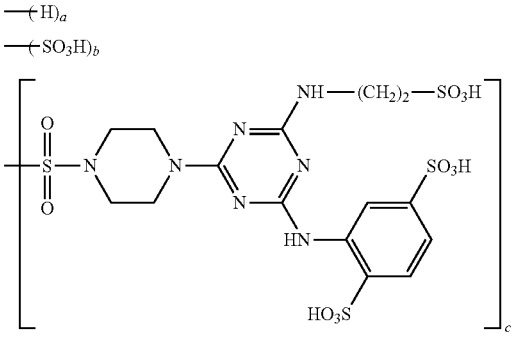 | $0 \leq a \leq 1$<br>$0 \leq b \leq 2$<br>$1 \leq c \leq 3$<br>$1 \leq b + c \leq 3$ |
| 40 | —(H)$_a$<br>—(SO$_3$H)$_b$<br>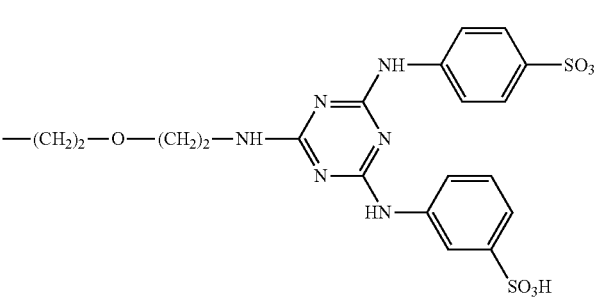 | $0 \leq a \leq 1$<br>$0 \leq b \leq 2$<br>$1 \leq c \leq 3$<br>$1 \leq b + c \leq 3$ |

TABLE 9

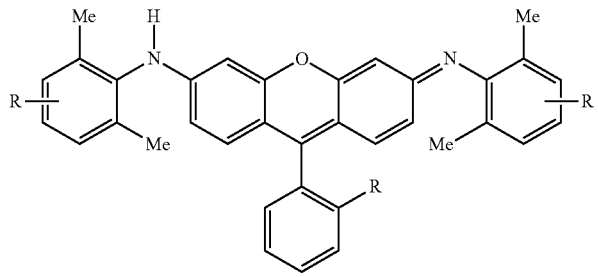

| Exemplarly Compound | R | |
|---|---|---|
| 41 | —(H)$_a$ —(SO$_3$H)$_b$ [complex structure with sulfonamide-piperazine-triazine bearing NH—(CH$_2$)$_2$—SO$_3$H and NH-(2,5-disulfophenyl) substituents]$_c$ | 0 ≤ a ≤ 1<br>0 ≤ b ≤ 2<br>1 ≤ c ≤ 3<br>1 ≤ b + c ≤ 3 |
| 42 | —(H)$_a$ —(SO$_3$H)$_b$ [sulfonamide-(CH$_2$)$_3$-NH-triazine bearing NH-(4-sulfophenyl) and NH-(3-sulfophenyl) substituents]$_c$ | 0 ≤ a ≤ 1<br>0 ≤ b ≤ 2<br>1 ≤ c ≤ 3<br>1 ≤ b + c ≤ 3 |
| 43 | —(H)$_a$ —(SO$_3$H)$_b$ [sulfonyl-(2,5-dimethylpiperazine)-triazine bearing NH—(CH$_2$)$_2$—SO$_3$H and NH-(2,5-disulfophenyl) substituents]$_c$ | 0 ≤ a ≤ 1<br>0 ≤ b ≤ 2<br>1 ≤ c ≤ 3<br>1 ≤ b + c ≤ 3 |

TABLE 9-continued

| Exemplarly Compound | R | |
|---|---|---|
| 44 | —(H)$_a$ —(SO$_3$H)$_b$ [sulfonamide-triazine structure with NH-phenyl-SO$_3$H and NH-phenyl-SO$_3$H groups]$_c$ | $0 \leq a \leq 1$ $0 \leq b \leq 2$ $1 \leq c \leq 3$ $1 \leq b + c \leq 3$ |
| 45 | —(H)$_a$ —(SO$_3$H)$_b$ [sulfonamide-piperazine-triazine structure with NH—(CH$_2$)$_2$—SO$_3$H and NH-phenyl-(SO$_3$H)$_2$ groups]$_c$ | $0 \leq a \leq 1$ $0 \leq b \leq 2$ $1 \leq c \leq 3$ $1 \leq b + c \leq 3$ |

TABLE 10

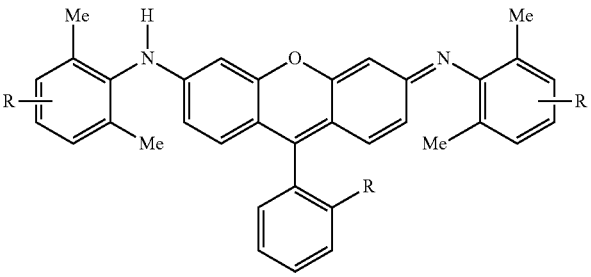

| Exemplarly Compound | R | |
|---|---|---|
| 46 | —(H)$_a$<br>—(SO$_3$H)$_b$<br>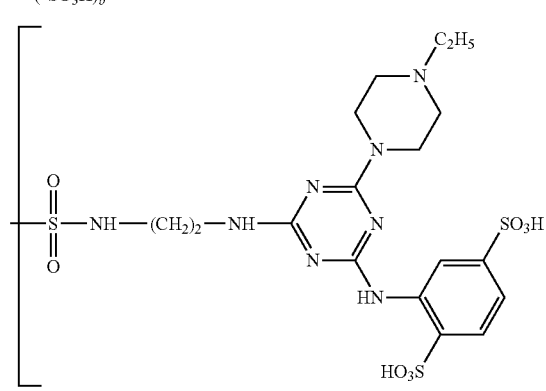 | 0 ≤ a ≤ 1<br>0 ≤ b ≤ 2<br>1 ≤ c ≤ 3<br>1 ≤ b + c ≤ 3 |
| 47 | —(H)$_a$<br>—(SO$_3$H)$_b$<br>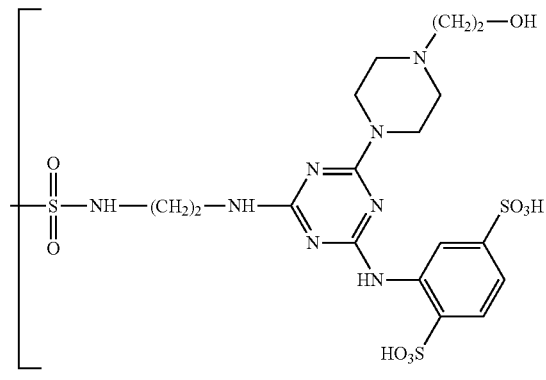 | 0 ≤ a ≤ 1<br>0 ≤ b ≤ 2<br>1 ≤ c ≤ 3<br>1 ≤ b + c ≤ 3 |

A synthesis method of the compound of the present invention is not particularly limited, but for example, it is possible to use a method described in [0.154] to [0169] of Japanese Patent Application Laid-Open No. 2010-254964.

[Coloring Composition]

A coloring composition of the present invention contains at least one kind of compound represented by Formula (1) of the present invention. The coloring composition of the present invention may contain a medium, and the case of using a solvent as the medium is suitable particularly as an inkjet ink. The coloring composition of the present invention may be manufactured by using a lipophilic medium or an aqueous medium as a medium, and dissolving and/or dispersing the compound of the present invention in the medium. The coloring composition of the present invention is preferably a ease of using an aqueous medium. An ink composition except for the medium is also included in the coloring composition of the present invention.

In the present invention, the content of the compound of the present invention included in the coloring composition is determined according to the kind, of substituent in Formula (1) to be used and the kind of solvent component used to manufacture the coloring composition, but the content of the compound represented by Formula (1) or the salt thereof in the coloring composition is preferably 1 to 10% by mass and more preferably 2 to 6% by mass, based on the total mass of the coloring composition.

Chromogenic property of ink on a recording medium when printed may be improved by setting the content of the compound represented by Formula (1), which is included in the coloring composition to 1% by mass or more, and a desired image concentration may be secured. In addition, a discharge property of the coloring composition used in the inkjet recording method may be improved by setting the total amount of the compound represented by Formula (1), which is included in the coloring composition to 10% by mass or less, and furthermore, an effect such as prevention of an inkjet nozzle from being clogged, and the like is obtained.

The coloring composition of the present invention may contain other additives if necessary, within a range not impairing the effect of the present invention. Examples of the other additives include additives which may be used in the inkjet ink to be described below.

[Inkjet Ink]

Next, the inkjet ink of the present invention will be described.

The present invention also relates to an inkjet ink containing the coloring composition of the present invention (more specifically, inkjet recording ink).

The inkjet ink may be manufactured by dissolving and/or dispersing the compound (mixture) of the present invention in a lipophilic medium or an aqueous medium. The inkjet ink is preferably an ink manufactured by using an aqueous medium.

If necessary, other additives are contained within a range not impairing the effect of the present invention. Examples of the other additives include publicly known additives such as a drying inhibitor (wetting agent), a discoloration inhibitor, an emulsification stabilizer, a permeation accelerator, an ultraviolet absorbent, an antiseptic, a fungicide, a adjusting agent, a surface tension adjusting agent, a defoaming agent, a viscosity adjusting agent, a dispersing agent, a dispersion stabilizer, a rust inhibitor and a chelating agent. These various additives are directly added to the ink solution in the case of a water-soluble ink. When an oil-soluble dye is used in the form of a dispersion, the additives are generally added to the dispersion after the preparation of a dye dispersion, but may be added to the oil or aqueous phase during the preparation.

The drying inhibitor is suitably used for the purpose of preventing occurrence of clogging due to drying of a corresponding inkjet ink, at an ink jetting port of a nozzle used for the inkjet recording system.

The drying inhibitor is preferably a water-soluble organic solvent having a vapor pressure lower than that of water. Specific examples thereof include polyhydric alcohols represented by ethylene glycol, propylene glycol, diethylene glycol, polyethylene glycol, thiodiglycol, dithiodiglycol, 2-methyl-1,3-propanediol, 1,2,6-hexanetriol, an acetylene glycol derivative, glycerin and trimethylolpropane, and the like, lower alkyl ethers of polyhydric alcohol, such as ethylene glycol monomethyl(or ethyl)ether, diethylene glycol monomethyl(or ethyl)ether and triethylene glycol monoethyl (or butyl)ether, heterocyclic rings such as 2-pyrrolidone, N-methyl-2-pyrrolidone, 1,3-dimethyl-2-imidazolidinone and N-ethylmorpholine; sulfur-containing compounds such as sulfolane, dimethylsulfoxide and 3-sulfolene, polyfunctional compounds such as diacetone alcohol and diethanolamine, and urea derivatives. Among them, polyhydric alcohols such as glycerin and diethylene glycol are more preferred. Furthermore, the aforementioned drying inhibitors may be used either alone or in combination of two or more thereof. The drying inhibitor is preferably contained in an amount from 10 to 50% by mass in the ink.

The permeation accelerator is suitably used for the purpose of permeating the inkjet ink well into paper. As the permeation accelerator, it is possible to use alcohols such as ethanol, isopropanol, butanol, di(tri)ethylene glycol monobutyl ether, and 1,2-hexanediol, sodium lauryl sulfate, sodium oleate, a non-ionic surfactant, and the like. When the aforementioned permeation accelerator is contained in the amount from 5 to 30 mass % in the ink, typically there is a sufficient effect, and it is preferable to use the permeation accelerator within an addition amount range that does not causes bleeding of a printed letter and print through.

The ultraviolet absorbent is used for the purpose of enhancing storage property of an image. As the ultraviolet absorbent, it is also possible to use benzotriazole-based compounds described in Japanese Patent Application Laid-Open Nos. S58-185677, S61-190537, H2-782, H5-197075 and H9-34057, and the like, benzophenone-based compounds described in Japanese Patent Application Laid-Open Nos. 546-2784 and H5-194483 and U.S. Pat. No. 3,214,463, cinnamic acid-based compounds described in Japanese Examined Patent Application Publication Nos. 548-30492 and 556-21141 and Japanese Patent Application Laid-Open No. 510-88106, and the like, triazine-based compounds described in Japanese Patent Application Laid-Open Nos. H4-298503, H8-53427, H8-239368, and H10-182621 and Japanese Unexamined Patent Application Publication No. H8-501291, and the like, compounds described in Research Disclosure No. 24239, and compounds represented by a stilbene-based compound and a benzoxazole-based compound, which absorbs ultraviolet light to emit fluorescent light, so-called fluorescent brightening agents.

The discoloration inhibitor is used for the purpose of enhancing storage property of an image. As the discoloration inhibitor, various organic and metal complex-based discoloration inhibitors may be used. Examples of the organic discoloration inhibitor include hydroquinones, alkoxyphenols, dialkoxyphenols, phenols, anilines, amines, indanes, cromanes, alkoxyanilines, heterocyclics and the like, and examples of the metal complex include a nickel complex, a zinc complex, and the like. More specifically, it is possible to use compounds described in the patents cited in VII-I to VII-J of Research Disclosure No. 17643, Research Disclosure No. 15162, the left column on page 650 of Research Disclosure No. 18716, page 527 of Research Disclosure No. 36544, page 872 of Research Disclosure No. 307105 and Research Disclosure No. 15162, or compounds included in formulae and compound examples of representative compounds described on pages 127 to 137 of Japanese Patent Application Laid-Open No. S62-215272.

Examples of the fungicide include sodium dehydroacetate, sodium benzoate, sodium pyridinethione-1-oxide, p-hydroxybenzoate ethyl ester, 1,2-benzisothiazolin-3-one, salts thereof and the like. The fungicide is preferably used in an amount of 0.02 to 1.00% by mass in the ink.

As the pH adjusting agent, the neutralizer (organic base, inorganic alkali) may be used. For the purpose of enhancing storage stability to an inkjet ink, it is more preferred that the pH adjusting agent is added so that corresponding inkjet ink has a pH of preferably 6 to 10, and more preferably 7 to 10.

Examples of the surface tension adjusting agent include non-ionic, cationic or anionic surfactants. Further, the surface tension of the inkjet ink, of the present invention is preferably 25 to 70 mN/m. In addition, the value is preferably 25 to 60 mN/m. Furthermore, the viscosity of the inkjet ink of the present invention is preferably 30 mPa·s or less. Further, the viscosity thereof is preferably adjusted to 20 mPa·s or less. Preferred examples of the surfactant include anionic surfactants such as fatty acid salt, alkyl ester sulfate, alkylbenzene sulfonate, alkylnaphthalene sulfonate, dialkyl sulfosuccinate, alkyl ester phosphate, naphthalene sulfonic acid formaline condensate, and polyoxyethylenealkyl ester sulfate, and non-ionic surfactants such as polyoxyethylene alkyl ether, polyoxyethylene alkylallyl ether, polyoxyethylene fatty acid ester, sorbitan fatty acid ester, polyoxyethylene sorbitan fatty acid ester, polyoxyethylene alkylamine, glycerin fatty acid ester and an oxyethyleneoxypropylene block copolymer. In addition, SURFYNOLS (Air Products & Chemicals Inc.) that is an acetylene-based polyoxyethylene oxide surfactant is also preferably used. Furthermore, amine oxide type amphoteric surfactants such as N,N-dimethyl-N-alkylamine oxide are also preferred. Furthermore, it is also possible to use a surfactant exemplified as the surfactants described on pages (37) and (38) of Japanese Patent Application Laid-Open No. 559-157,636 and Research Disclosure No. 308119 (1989).

As the defoaming agent, a chelating agent represented by fluorine- or silicon-based compounds or EDTA may also be used, if necessary.

When the compound of the present invention is dispersed in an aqueous medium, it is preferred that a colored particle containing the compound and an oil-soluble polymer is dispersed in an aqueous medium, as described in Japanese Patent Application Laid-Open No, H11-286637 and Japanese Patent Application Nos. 2000-78491, 2000-80259 and 2000-62370, or the compound of the present invention dissolved in a high-boiling point organic solvent is dispersed in an aqueous medium as described in Japanese Patent Application Nos. 2000-78454, 2000-78491, 2000-203856 and 2000-203857. As for a specific method of dispersing the compound of the present invention in an aqueous medium, an oil-soluble polymer to be used, a high-boiling point organic solvent, an additive and a use amounts thereof, those described in the patent documents and the like may be preferably used. Otherwise, the compound of the present invention may be dispersed in a particle state while being a solid. At the time of dispersing, a dispersing agent or a surfactant may be used. As the dispersing device, it is possible to use a simple stirrer, an impeller stirring system, an in-line stirring system, a mill system (for example, colloid mill, ball mill, sand mill, attritor, roll mill, agitator mill and the like), an ultrasonic system, and a high-pressure emulsion dispersion system (high-pressure homogenizer: as a specific commercially available device, Gaulin homogenizer, MICROFLUIDIZER, DeBEE 2000 and the like). Methods for preparing the aforementioned inkjet ink are described in detail in Japanese Patent Application Laid-Open Nos. H5-148436, H5-295312, H7-97541, H7-82515, H7-118584 and H11-286637 and Japanese Patent Application No, 2000-87539 in addition to the aforementioned patent documents, and may also be used for the preparation of the inkjet ink of the present invention.

As the aqueous medium, it is possible to use a mixture that contains water as a major component and, if desired, a water-miscible organic solvent added. Examples of the water-miscible organic solvent include alcohol (for example, methanol, ethanol, propanol, isopropanol, butanol, isobutanol, sec-butanol, t-butanol, pentanol, hexanol, cyclohexanol and benzylalcohol), polyhydric alcohols (for example, ethylene glycol, diethylene glycol, triethylene glycol, polyethylene glycol, propylene glycol, dipropylene glycol, polypropylene butylene glycol, hexanediol, pentanediol, glycerin, hexanetriol and thiodi glycol), a glycol derivative (for example, ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monomethyl ether and ethylene glycol monophenyl ether), amine (for example, ethanolamine, diethanolamine, triethanolamine, N-methyldiethanolamine, N-ethyldiethanolamine, morpholine. N-ethylmorpholine, ethylenediamine, diethylenetriamine, triethylenetetramine, polyethyleneimine and tetramethylpropylenediamine), and other polar solvents (for example, formamide, N,N-dimethylformamide, N,N-dimethylacetamide, dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile and acetone). Further, the water-miscible organic solvents may be used in combination of two or more kinds thereof.

The compound of the present invention is contained in an amount of preferably 0.2 parts by mass to 10 parts by mass and more preferably 1 part by mass to 6 parts by mass, in 100 parts by mass of the inkjet ink of the present invention. In addition, other colorants may be used in combination with the compound of the present invention in the inkjet ink of the present invention. When two or more colorants are used in combination, it is preferred that the sum of the contents of the colorants is in the aforementioned range.

The viscosity of the inkjet ink of the present invention is preferably 30 mPa·s or less. In addition, the surface tension thereof is preferably 25 mN/m to 70 mN/m. The viscosity and the surface tension may be adjusted by adding various additives, for example, a viscosity adjusting agent, a surface tension adjusting agent, a specific resistance adjusting agent, a film adjusting agent, an ultraviolet absorbent, an antioxidant, a discoloration inhibitor, a fungicide, a rust inhibitor, a dispersing agent and a surfactant.

The inkjet ink of the present invention may be used for forming a full-color image as well as a monochromatic image. In order to form a full-color image, a magenta tone ink, a cyan tone ink and a yellow tone ink may be used, and in order to adjust the tone, a black tone ink may be further used.

As an applicable yellow dye, any dye may be used. For example, examples thereof include an aryl or heterylazo dye having heterocyclic rings such as phenols, naphthols, anilines, pyrazolones or pyridones, or open chain-type active methylene compounds as a coupling component (hereinafter, referred to as a coupler component); for example, an azomethine dye having open chain-type active methylene compounds and the like as the coupler component; for example, a methine dye such as a benzylidene dye or a monomethineoxonol dye; and for example, a quinone-based dye such as a naphthoquinone dye and an anthraquinone dye, and the like, and examples of the other dyes may include a quinophthalone dye, nitro and nitroso dyes, an acridine dye, an acridinone dye and the like.

As an applicable magenta dye, any dye may be used. Examples thereof include an aryl or heterylazo dye having phenols, naphthols, anilines and the like as the coupler component; for example, an azomethine dye having pyrazolones, pyrazolotriazoles and the like as the coupler component; for example, a methine dye such as an arylidene dye, a styryl dye, a melocyanine dye, a cyanine dye and an oxonol dye; a carbonium dye such as a diphenylmethane dye, a triphenylmethane dye and a xanthene dye; for example, a quinone dye such as naphthoquinone, anthraquinone and anthrapyridone; and for example, a condensated polycyclic dye such as a dioxazine dye, and the like.

As an applicable cyan dye, any dye may be used. Examples thereof include an aryl or heterylazo dye having phenols, naphthols, anilines and the like as the coupler component; for example, an azomethine dye having heterocyclic rings and the like such as phenols, naphthols and pyrrolotriazole as the coupler component; a polymethine dye such as a cyanine dye, an oxonol dye and a melocyanine dye; a carbonium dye such as a diphenylmethane dye, a triphenylmethane dye and a xanthene dye; a phthalocyanine dye; an anthraquinone dye; indigo and thioindigo dyes and the like.

These dyes may be dyes that exhibit the colors yellow, magenta and cyan initially after a part of the chromophore is dissociated, and in that case the counter cation may be an inorganic cation such as an alkali metal or ammonium, and an organic cation such pyridinium and a quaternary ammonium salt, and furthermore, may be a polymer cation having these metals and salts in the partial structure thereof.

Examples of an applicable black material which may be applied include a dispersion of carbon black in addition to disazo, trisazo and tetraazo dyes.

The ink composition of the present invention may be used in recording methods such as printing, copying, marking, writing, drafting and stamping, and is particularly suitable for use in the inkjet recording method.

[Inkjet Recording Method]

The present invention also relates to an inkjet recording method of forming an image by using the coloring composition or inkjet ink of the present invention.

The inkjet recording method of the present invention donates energy to the inkjet ink to form an image on a publicly known image-receiving material, that is, a plain paper, a resin coated-paper, an inkjet exclusive paper, for example, film, electronic and photo paper, fabric, glass, metal, ceramics and the like described in Japanese Patent Application Laid-Open Nos. H8-169172, H8-27693, H2-276670, 117-276789, 119-323475, S62-238783, H10-153989, H10-217473, H10-235995, 1110-337947, H10-217597, H10-337947 and the like.

When an image is formed, a polymer particle dispersion (also referred to as a polymer latex) may be used in combination for the purpose of imparting glossiness or water resistance or improving weather resistance. A time point when a polymer latex is imparted to an image-receiving material may be before and after a coloring agent is imparted, or a simultaneous time point, and accordingly, a place where the polymer latex is added thereto may also be in the image-receiving paper or in an ink, or the polymer latex may be used alone as a liquid material. Specifically, it is possible to preferably use a method described in Japanese Patent Application Nos. 2000-363090, 2000-315231, 2000-354380, 2000-343944, 2000-268952, 2000-299465, 2000-297365 and the like.

Hereinafter, a recording paper and a recording film to be used to perform inkjet printing using ink of the present invention will be described.

In the recording paper and the recording film, a support is formed of a chemical pulp such as LBKP and NBKP, a mechanical pulp such as GP, PGW, RMP, TMP, CTMP, CMP and COP, a used-paper pulp such as DIP, and the like, and if necessary, it is possible to use a support manufactured by various kinds of devices such as a Fourdrinier paper machine and a cylinder paper machine by mixing publicly known additives in the related art, such as a pigment, a hinder, a sizing agent, a fixing agent, a cationic agent and a paper strengthening agent. In addition to such supports, any of synthetic paper or plastic film sheet may be used, and it is preferred that the support has a thickness of 10 μm to 250 μm and a basis weight of 10 g/m² to 250 g/m².

An ink-receiving layer and a back coat layer may be formed as they are on the support, or after a size press or an anchor coat layer is formed of starch, polyvinyl alcohol and the like, the ink-receiving layer and the back coat layer may be formed. Further, the support may be subjected to planarization treatment by a calendar device such as a machine calendar, a TG calendar and a soft calendar. In the present invention, paper and plastic films in which polyolefins (for example, polyethylene, polystyrene, polyethylene terephthalate, polybutene and a copolymer thereof) are laminated on both surfaces thereof are more preferably used as the support.

It is preferred that a white pigment (for example, titanium oxide and zinc oxide) or a tinting dye (for example, cobalt blue, ultramarine blue and neodymium oxide) is added to polyolefins.

A pigment or an aqueous binder is contained in an ink-receiving layer to be formed on a support. As a pigment, a white pigment is preferred, and examples of the white pigment include an white inorganic pigment such as calcium carbonate, kaolin, talc, clay, diatomaceous earth, synthetic amorphous silica, aluminum silicate, magnesium silicate, calcium silicate, aluminum hydroxide, alumina, lithopone, zeolite, barium sulfate, calcium sulfate, titanium dioxide, zinc sulfide, and zinc carbonate, an organic pigment such as a styrene-based pigment, an acrylic pigment, a urea resin and a melamine resin, and the like. As a white pigment contained in an ink-receiving layer, a porous inorganic pigment is preferred, and a synthetic amorphous silica having a large pore area and the like are particularly suitable. As the synthetic amorphous silica, it is possible to use either a silicic acid anhydride obtained by a dry production method or a hydrated silicic acid obtained by a wet production method, but it is particularly preferred that a hydrated silicic acid is used.

Examples of the aqueous binder contained in the ink-receiving layer include a water-soluble polymer such as polyvinyl alcohol, silanol modified polyvinyl alcohol, starch, cationized starch, casein, gelatin, carboxymethyl cellulose, hydroxyethyl cellulose, polyvinylpyrrolidone, polyalkylene oxide and a polyalkylene oxide derivative, a water-dispersible polymer such as a styrenebutadiene latex and an acryl emulsion, and the like. These aqueous binders may be used either alone or in combination of two or more kinds or thereof. In the present invention, among the polymers, polyvinyl alcohol or silanol modified polyvinyl alcohol is particularly suitable in view of adhesion property to a pigment and peeling resistance of an ink-receiving layer.

The ink-receiving layer may contain a mordant, a water-resistant agent, a light fastness enhancer, a surfactant and other additives in addition to the pigment and the aqueous binder.

It is preferred that the mordant added to the ink-receiving layer is immobilized. To this end, a polymer-mordant is preferably used.

The polymer-mordant is described in Japanese Patent Application Laid-Open Nos. S48-28325, S54-74430, S54-124726, S55-22766, S55-142339, S60-23850, S60-23851, S60-23852, S60-23853, S60-57836, S60-60643, S60-118834, S60-122940, S60-122941, S60-122942, S60-235134 and H1-161236 and U.S. Pat. Nos. 2,484,430, 2,548,564, 3,148,061, 3,309,690, 4,115,124, 4,124,386, 4,193,800, 4,273,853, 4,282,305 and 4,450,224. Particularly preferred is an image-receiving material containing a polymer-mordant described on pages 212 to 215 of Japanese Patent Application Laid-Open No. 111-161236. When the polymer-mordant described in the patent document is used, an image having excellent image quality is obtained, and light fastness of the image is improved.

The water-resistant agent is effective for water-resisting an image, and as the water-resistant agent, a cationic resin is particularly preferred. Examples of the cationic resin include polyamide polyamine epichlorohydrin, polyethyleneimine, polyamine sulfone, dimethyldiallylammonium chloride polarized product, cation polyacrylamide, colloidal, silica and the like, and among the cationic resins, polyamide polyamine epichlorohydrin is particularly suitable. The content of the cation resin is preferably 1 to 15% by mass and particularly preferably 3 to 10% by mass based on the total solid content of the ink-receiving layer.

Examples of the light fastness enhancer include zinc sulfate, zinc oxide, hindered amine-based antioxidants, benzotriazole-based ultraviolet absorbents such as benzophenone, and the like. Among these, zinc sulfate is suitable.

The surfactant functions as a coating aid, a peeling property improver, a sliding property improver or an antistatic agent. The surfactant is described in Japanese Patent Application Laid-Open Nos. S62-173463 and S62-183457. Instead of the surfactant, an organic fluoro compound may be used. It is preferred that the organic fluoro compound is hydrophobic. Examples of the organic fluoro compound include a fluorine-based surfactant, an oily fluorine-based compound (for example, fluorine oil) and a solid fluorine compound resin (for example, ethylene tetrafluoride resin). The organic fluoro compound is described in Japanese Examined Patent Application Publication No. S57-9053 (columns 8 to 17) and Japanese Patent Application Laid-Open Nos. 6'-20994 and S62-135826. Examples of other additives added to the ink-receiving layer include a pigment dispersant, a thickener, a defoaming agent, a dye, a fluorescent brightening agent, an antiseptic, a pH controlling agent, a matting agent, a film hardening agent and the like. Further, the ink-receiving layer may have one layer or two layers.

A back coat layer may also be formed on the recording paper and the recording film, and examples of the component that may be added to the layer include a white pigment, an aqueous binder, or other components. Examples of a white pigment contained in the back coat layer include white inorganic pigments such as light calcium carbonate, heavy calcium carbonate, kaolin, talc, calcium sulfate, barium sulfate, titanium dioxide, zinc oxide, zinc sulfide, zinc carbonate, satin white, aluminum silicate, diatomaceous earth, calcium silicate, magnesium silicate, synthetic amorphous silica, colloidal silica, colloidal alumina, pseudo-boehmite, aluminum hydroxide, alumina, lithopone, zeolite, hydrolyzed halloysite, magnesium carbonate and magnesium hydroxide, and organic pigments such as styrene-based plastic pigment, acrylic plastic pigment, polyethylene, microcapsule, urea resin and melamine resin.

Examples of the aqueous binder contained in the back coat layer include water-soluble polymers such as styrene/maleate copolymer, styrene/acrylate copolymer, polyvinyl alcohol, silanol modified polyvinyl alcohol, starch, cationized starch, casein, gelatin, carboxymethyl cellulose, hydroxyethyl cellulose and polyvinylpyrrolidone, and water-dispersible polymers such as styrene butadiene latex and acryl emulsion. Examples of other components contained in the back coat layer include a defoaming agent, a foam inhibitor, a dye, a fluorescent brightening agent, an antiseptic, a water-resistant agent and the like.

A polymer latex may be added to a constituent layer (including the back coat layer) of the inkjet recording paper or the recording film. The polymer latex is used for the purpose of improving film physical properties, such as stabilizing the dimension and preventing curling, adhesion or film cracking. The polymer latex is described in Japanese Patent Application Laid-Open Nos. S62-245258, S62-1316648 and S62-110066. When a polymer latex having a low glass transition temperature (40° C. or less) is added to a layer including a mordant, cracks or curling of the layer may be prevented. In addition, even when a polymer latex having a high glass transition temperature is added to the back coat layer, curling may be prevented.

The ink of the present invention has no limitation on the recording system of the inkjet, and is used in a known system, for example, a charge control system of discharging an ink using an electrostatic attraction force, a drop-on-demand system (pressure pulse system) using the oscillating pressure of a piezoelectric element, an acoustic inkjet system of discharging ink by converting electrical signals into acoustic beams to irradiate the ink with the acoustic beams and using radiation pressure, a thermal inkjet system of using pressure produced by heating ink to form bubbles, and the like. Examples of the inkjet recording method include a system of ejecting a large number of small volumes of ink with a low concentration, which is called photo-ink, a system of improving the image quality by using a plurality of inks having substantially the same hue but different concentrations, or a system of using colorless and transparent ink.

[Color Filter]

The present invention also relates to a color filter containing the compound represented by Formula (1).

As a method for forming a color filter, there is a method of first forming a pattern by a photoresist and then continuously performing dyeing, or a method of forming a pattern by a photoresist added with a colorant, as disclosed in Japanese Patent Application Laid-Open Nos. H4-163552, H4-128703 and H4-175753. As a method to be used in the case of introducing the compound of the present invention into a color filter, any of these methods may be used, but examples of a preferred method include a method of forming a color filter, which includes applying a positive-type resist composition containing a thermosetting resin, a quinonediazide compound, a crosslinking agent, a colorant, and a solvent on a substrate, exposing the applied composition through a mask, developing the corresponding exposed portion to form a positive-type resist pattern, entirely exposing the positive-type resist pattern, and then curing the positive-type resist pattern after the exposure, as described in Japanese Patent Application Laid-Open No. 114-175753 or 116-35182. Further, an ROB primary color-based color filter or a YMC complementary color-based color filter may be obtained by forming a black matrix according to a typical method. Even in the case of the color filter, the amount of the compound of the present invention to be used is not limited, but is preferably 0.1% by mass to 50% by mass.

For the thermosetting resin, the quinonediazide compound, the crosslinking agent, and the solvent, which are used at this time, and the amounts thereof to be used, those which are described in the aforementioned patent documents may be preferably used.

[Color Toner]

The present invention also relates to a color toner containing the compound represented by Formula (1).

The content of the compound of the present invention in 100 parts by mass of a color toner is not particularly limited, but is preferably 0.1 part by mass or more, more preferably 1 part by mass to 20 parts by mass, and most preferably 2 parts by mass to 10 parts by mass. As a binder resin for a color toner, into which the compound of the present invention is to be introduced, all binders which are generally used may be used.

Examples thereof include styrene-based resin-acrylic resin-styrene/acrylic resin-polyester resin and the like.

For the purpose of improving flowability, controlling electrostatic charge and the like with respect to a toner, inorganic fine powders or organic particles may be externally added to the toner. Silica particles and titania particles surface-treated with a coupling agent containing an alkyl group and the like are preferably used. Further, these particles have a number average primary particle size of preferably 0 nm to 500 nm, and are added in an amount of preferably 0.1% by mass to 20% by mass to the toner.

As a release agent, all release agents used in the related art may be used. Specific examples thereof include olefins such as low molecular polypropylene-low molecular polyethylene-ethylene-propylene copolymer, and microcrystalline-wax-carnauba wax-sazol wax-paraffin wax and the like. The addition amount thereof is preferably 1% by mass to 5% by mass in the toner.

The charge controlling agent may be added, if necessary, but is preferably colorless from the viewpoint of chromogenic properties. Examples thereof include those of a quaternary ammonium salt structure, those of a calixarene structure and the like.

As a carrier, it is possible to use any of the non-coated carriers constituted by particles of magnetic material such as iron or ferrite alone, and resin-coated carriers comprising magnetic material particles of which the surface is coated with a resin and the like. The average particle diameter of the carrier is preferably 30 μm to 150 μm in terms of volume average particle diameter.

The image forming method to which the toner is applied is not particularly limited, but examples thereof include a method of forming an image by repeatedly forming a color image on a photoreceptor, and then transferring the color image on the photoreceptor, a method of forming a color image by successively transferring an image formed on a photoreceptor onto an intermediate transfer body and the like, forming a color image on the intermediate transfer body and the like, and then transferring the color image onto an image-forming member such as paper, and the like.

EXAMPLES

Hereinafter, a synthesis method of the compound (mixture) of the present invention will be described in detail in Examples, but the present invention is not limited to these Examples at all. Unless otherwise indicated, "%" and "parts" in the Examples are % by mass and parts by mass.

SYNTHESIS EXAMPLE

Synthesis Example 1

Synthesis of Exemplary Compound 1 (b=0.5, c=1.5)

(Synthesis of Intermediate A)

27.6 g of cyanuric chloride, 100 g of iced water and 5 drops of calsolene oil were mixed in a 1,000 mL flask, and stirred. Separately, a solution was obtained by dispersing 42.1 g of aniline-2,5-disulfonic acid monosodium in 150 g of water and dissolving the solution by adjusting the pH to 6 by means of a 2N aqueous sodium hydroxide solution, and the solution was slowly added to the flask while maintaining the internal temperature at 5° C. or less. The reaction solution was allowed to react at room temperature for 2 hours while maintaining the pH at 4.5 using a 2N aqueous sodium hydroxide solution. Insoluble materials were removed by a GF/F filter manufactured by Whatman Inc., and then 16.8 g of dimethylamine was added thereto, and the resulting mixture was stirred at room temperature overnight. The reaction solution was warmed to an internal temperature of 40° C., 90 g of dimethylamine was added thereto, and the resulting mixture was allowed to react at 60° C. for 30 minutes. Sodium chloride corresponding to 10% of the total mass was added thereto, and the pH was adjusted to 1 using concentrated hydrochloric acid. The internal temperature was cooled to room temperature, and the precipitated crystals were filtered, sufficiently washed with a saturated saline solution and successively with acetone, and dried with an air blowing dryer at 60° C. overnight to obtain white crystal of Intermediate A. It was found that the compound had a purity of 82% (the other parts were assumed to be sodium chloride and water) based on the element analysis result.

(Synthesis of Exemplary Compound 1)

40 mL of thionyl chloride was added to a 100 mL flask, and stirred at room temperature. 3.4 g of C. I. Acid Red 289 (manufactured by Chugai Kasei Company Limited, Trade name CHUGAI AMINOL FAST PINK) was carefully and slowly added thereto, then 4 mL of DMF was added thereto, and the resulting mixture was stirred fin 90 minutes while increasing the internal temperature to 55° C. The reaction solution was cooled to room temperature and slowly added dropwise to 250 g of iced water in which 25 g of sodium chloride was dissolved, and the precipitated crystal was separated by filtration and washed with an ice-cold saturated saline solution to obtain a wet cake of Intermediate B.

2.56 g of Intermediate A was dispersed in 100 mL of water in a separate 500 mL flask, and dissolved by adjusting the pH to 8.5 by means of a 2N sodium hydroxide. The total amount of the wet cake of Intermediate B was added thereto. The pH was adjusted to 9.0 using sodium hydroxide, then, stirring was performed for 90 minutes by increasing the internal temperature to 50° C. while maintaining the pH at 9.0, and then stirring was performed overnight while adjusting the pH to 12. After confirming that the reaction solution was almost dissolved, the internal temperature was decreased to 30° C. and insoluble materials were removed by a qualitative filter paper manufactured by Whatman Inc., the pH of the aqueous solution obtained was adjusted to 8.0 using a hydrochloric acid water, and salt precipitation was performed by adding sodium chloride having a weight corresponding to 20% of the volume thereto. The precipitated crystal was separated by filtration and re-dissolved in 250 mL of water, the aqueous solution obtained was purified until electrical conductivity became 10 μS or less by dialysis, and then, after the aqueous solution was allowed to pass through a GET filter manufactured by Whatman Inc., the resulting mixture was completely solidified by removing moisture at 60° C. in an oven, thereby obtaining a metal gloss crystal of Exemplary Compound 1. Yield 3.4 g.

By an MS spectrum (m/z, nega), 1483 (M-H) and 741 (M-2H/2, 100%) corresponding to c=2, b=0 and 1068 (M-H) and 533 (M-2H/2) corresponding to c=1, b=1 were observed. In addition, from the analysis of the integration ratio by 1H NMR (DMSO-d6), it was assumed that about 1.5 triazine side chains had been introduced into the colorant site of Acid Red 289.

From the result, it is assumed that the present exemplary compound is a mixture of the following Exemplary Compounds 1a to 1f with b=0.5, c=1.5 in a ratio of h and c.

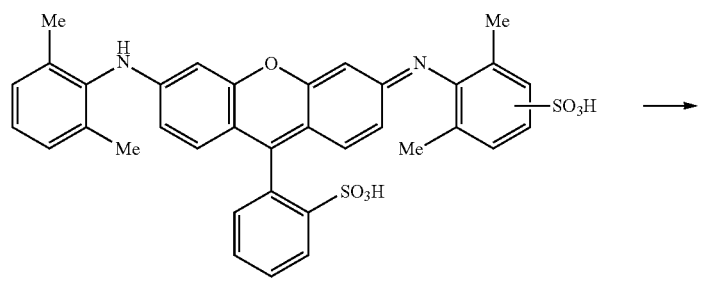
Acid Red 289
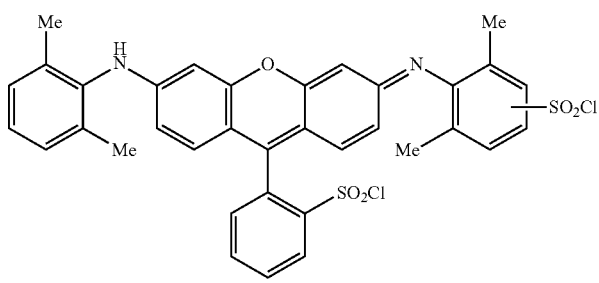
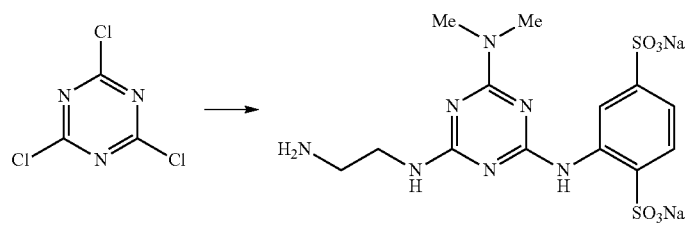
Intermediate A
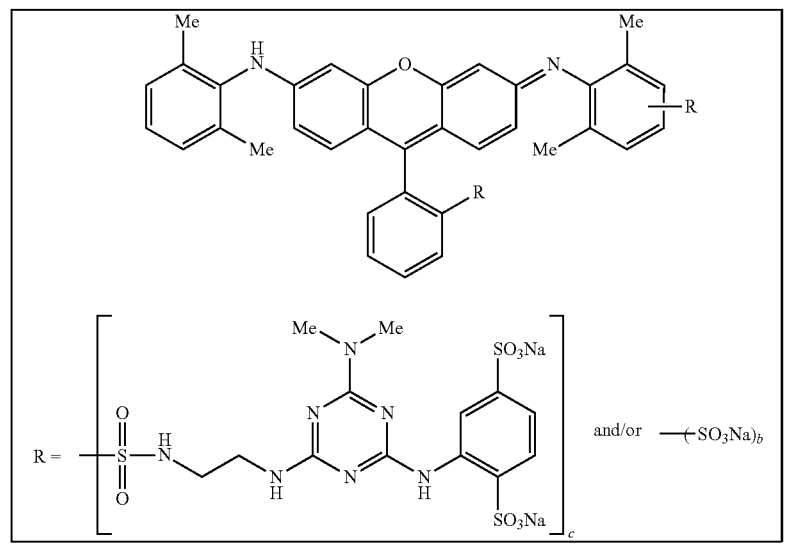
Exemplary Compound 1

-continued
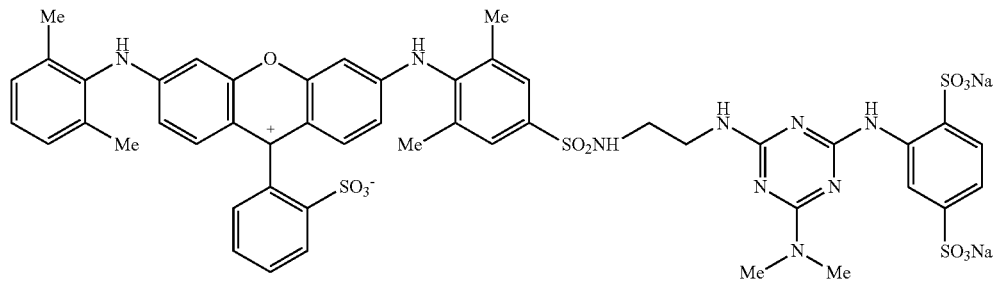
Exemplary Compound 1a
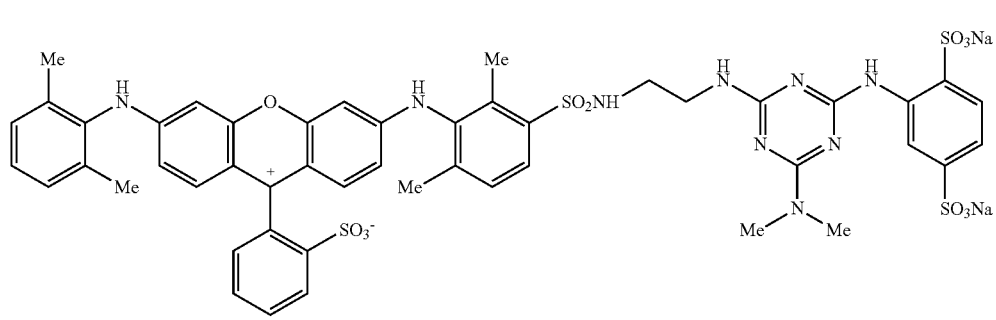
Exemplary Compound 1b
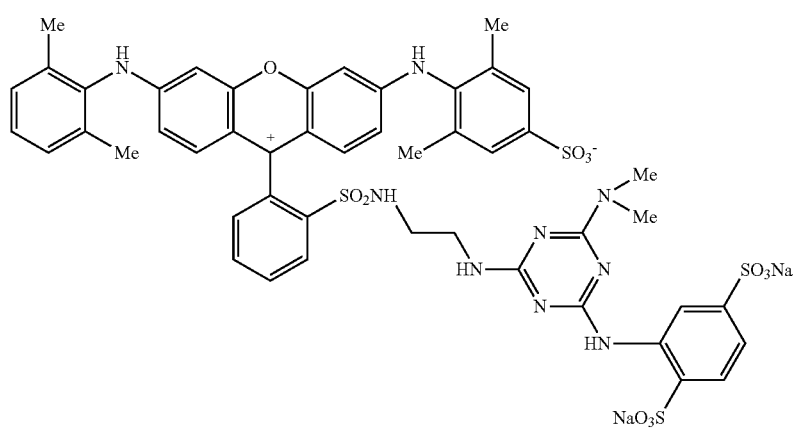
Exemplary Compound 1c
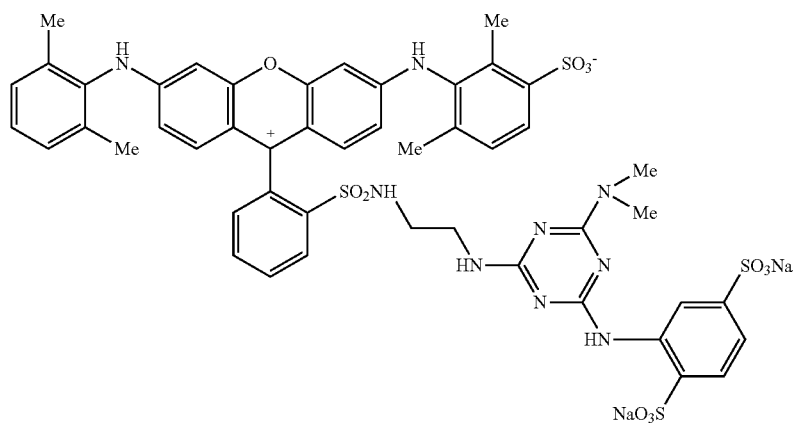
Exemplary Compound 1d -continued

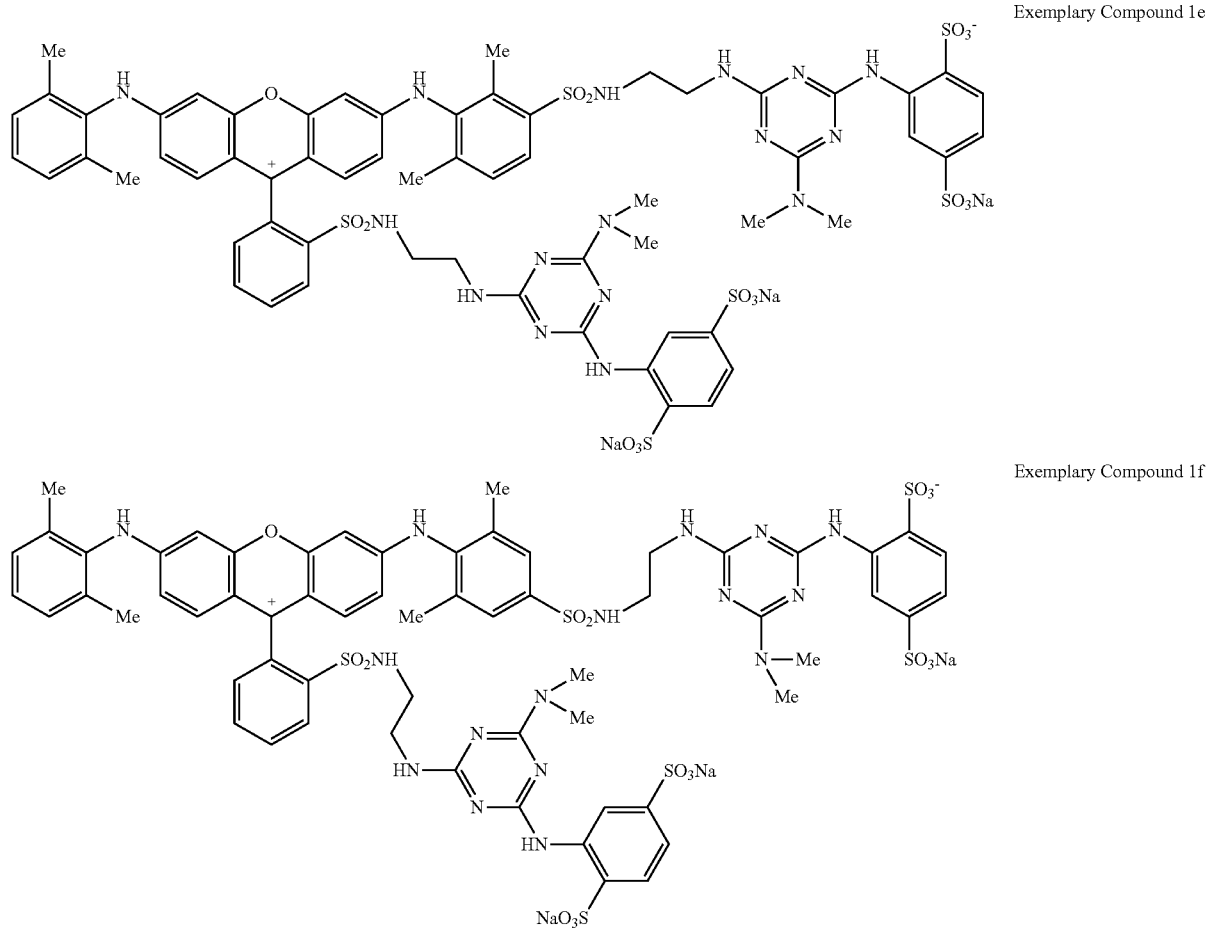

Exemplary Compound 1e

Exemplary Compound 1f

The other Exemplary Compounds (sodium salts) may also be synthesized in accordance with the above-described method.

Example 1

Deionized water was added to the following components to bring the total weight of the resulting mixture to 100 g, and then the mixture was stirred for 1 hour while being heated at 30° C. to 40° C. Thereafter, preparation was performed with KOH of 10 mol/L and pH=9, and a magenta ink solution was prepared by performing filtration under reduced pressure with a micro filter having an average pore diameter of 0.25 μm.

Composition of Ink Solution A:

| | |
|---|---|
| Colorant of the present invention (Exemplary Compound 1 (b = 0.5, c = 1.5)) | 3.50 g |
| Diethylene glycol | 10.65 g |
| Glycerin | 14.70 g |
| Diethylene glycol monobutyl ether | 12.70 g |
| Triethanolamine | 0.65 g |
| Olfine E1010 (manufactured by Nissin Chemical Industry Co., Ltd) | 0.9 g |

Ink Solutions B to E, and Ink Solutions F to I as ink solutions for comparison by using the following compounds were prepared in the same manner as in the preparation of Ink Solution A, except that the colorants were changed as shown in the following Table 11. Furthermore, the colorants used in Ink Solutions B to F were sodium salts of Exemplary Compounds described in the following Table 11.

TABLE 11

| Sample No. | Colorant | Ozone Resistance | Light Fastness | Moisture Resistance | Print Concentration |
|---|---|---|---|---|---|
| Ink Solution A | Exemplary Compound 1 (b = 0.5, c = 1.5) | A | A | A | A |
| Ink Solution B | Exemplary Compound 2 (b = 1, c = 1) | A | A | A | A |
| Ink Solution C | Exemplary Compound 3 (b = 1, c = 1) | A | A | A | A |
| Ink Solution D | Exemplary Compound 5 (b = 1, c = 1) | A | A | A | A |

TABLE 11-continued

| Sample No. | Colorant | Ozone Resistance | Light Fastness | Moisture Resistance | Print Concentration |
|---|---|---|---|---|---|
| Ink Solution E | Exemplary Compound 1 (b = 1, c = 1) | A | A | A | A |
| Ink Solution F | Comparative Compound 1 | B | B | C | A |
| Ink Solution G | Comparative Compound 2 | B | B | C | A |
| Ink Solution H | Comparative Compound 3 | C | C | A | A |
| Ink Solution I | Comparative Compound 4 | B | A | B | C |

Comparative Compound 1

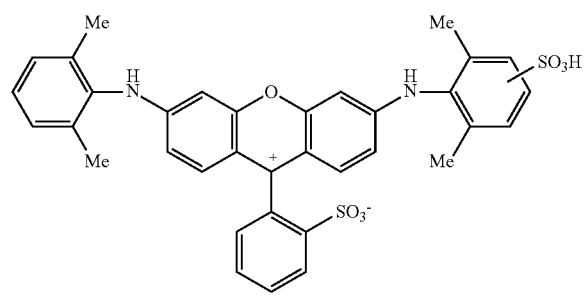

(C. I. Acid Red 289)

Comparative Compound 2

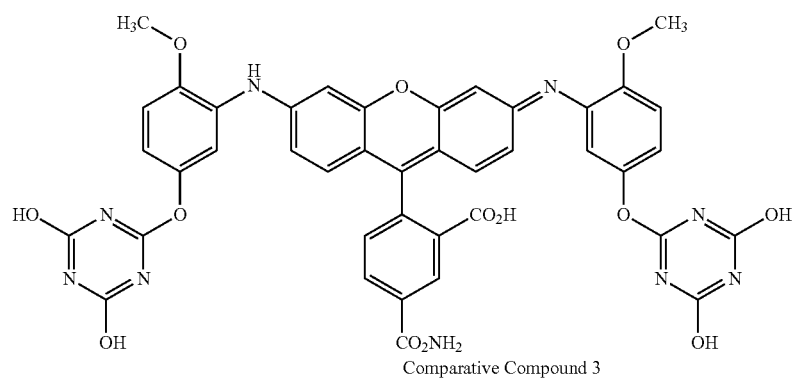

Comparative Compound 3

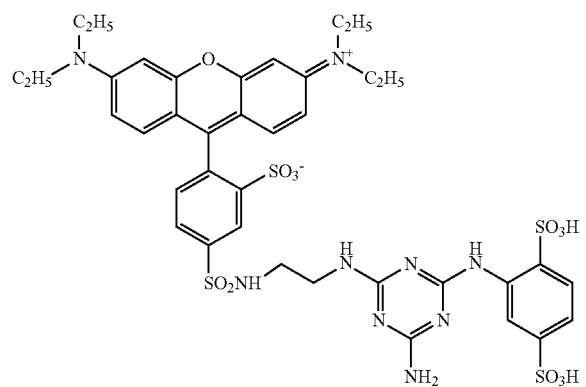

Comparative Compound 4

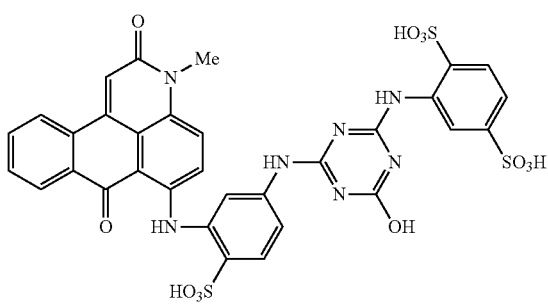

(Image Recording and Evaluation)

Inkjet inks of the Examples (ink Solutions A to E) and the Comparative Examples (ink Solutions F to I) described above were subjected to the following evaluations. The results are shown in Table 11.

Furthermore, in Table 11, ozone resistance, light fastness and moisture resistance were evaluated after each inkjet ink was used to record an image on a photo gloss paper (PM photo paper <Glossy> (KA420PSK, EPSON) manufactured by EPSON Co., Ltd.) by an inkjet printer (manufactured by EPSON Co., Ltd.; PM-700C). Print concentration was evaluated after each inkjet recording ink was used to record an image on a plain paper (plain paper (GF500, Canon) manufactured by Canon Inc.) by an inkjet printer (manufactured by EPSON Co., Ltd.; PM-700C).

<Ozone Resistance>

In a box which was set to an ozone gas concentration of 0.5±0.1 ppm, room temperature and dark place using a Siemens-type ozonizer to which an alternating current voltage of 5 kV was applied while passing dry air through the double glass tube thereof, the photo gloss paper having the image formed thereon was left to stand for 7 days, and the image concentration before and after standing under an ozone gas was measured by a reflection densitometer (X-Rite 310TR) and evaluated as a dye residual ratio. Further, the reflection concentration was measured at three points of 1, 1.5 and 2.0. The ozone gas concentration in the box was set using an ozone gas monitor (Model: OZG-EM-01) manufactured by APPLICS.

The evaluation was performed in a three-stage rating, in which A is a dye residual ratio of 70% or more at any concentration, 13 is less than 70% at one or two points, and C is less than 70% at all concentrations.

<Light Fastness>

After the image concentration Ci immediately after recording was measured, the image was irradiated with a xenon light (85,000 lux) for 7 days using a weather meter (Atlas C.165), then the image concentration Cf was measured and the dye residual ratio ($\{(Ci-Cf)/Ci\} \times 100\%$) was calculated from the difference between image concentrations before and after irradiation with the xenon light to perform evaluation. The image concentration was measured using a reflection densitometer (X-Rite 310TR).

The dye residual ratio was measured at three points of 1, 1.5 and 2.0 in reflection concentration. The evaluation was performed by a three-stage rating, in which A is a dye residual ratio of 80% or more at any concentration, 13 is less than 80% at one or two points, and C is less than 80% at all concentrations.

<Moisture Resistance>

During an inkjet recording, a check pattern (pattern obtained by alternately combining regular squares having a 1.5 mm angle at concentrations of 100% and 0%) was prepared, and a printed matter with a check pattern of magenta-white which was high in contrast was obtained. After printing, the printed matter with a check pattern, which had been dried for 24 hours, was left to stand under conditions of 80° C. and 70% RH for 3 days, and the degree of bleeding from a colored portion to a white portion was evaluated by the eyes to perform evaluation by a three-stage rating, in which A is the case where bleeding rarely occurs, B is the case where bleeding slightly occurs, and C is the case where bleeding clearly occurs.

<Print Concentration>

The print concentration scaled to 100% in print concentration was measured using a reflection densitometer (X-Rite 310TR), and the evaluation was performed by a three-stage rating, in which A is a print concentration of 2.2 or more, 13 is 2.0 or more and less than 2.2, and C is less than 2.0.

As clear from the results of Table 11, it can be seen that the ink of the Examples in which the dye of the present invention is used establishes performances such as ozone resistance, light fastness, moisture resistance and print concentration, and thus has very high performances as compared to each Comparative Example.

Example 2

Manufacture and Evaluation of Color Toner

<Manufacture of Color Toner>

3 parts by mass of the colorant of the present invention (Exemplary Compound 1 (b=0.5, c=1.5) and 100 parts by mass of a toner resin [styrene-acrylic acid ester copolymer; Himer TB-1000F (trade name, manufactured by Sanyo Chemical Industries, Ltd.)] were mixed and pulverized using a ball mill, then heated to 150° C. to conduct melt kneading and, after cooling the mixture, the mixture was coarsely crushed using a hammer mill, and then finely pulverized using a finely pulverizing machine based on an air jet system. The resultant particles were classified to select particles having a particle size of 1 μm to 20 μm, and a toner was prepared from the selected particles.

<Evaluation>

900 Parts by mass of a carrier iron powder (EFV250/400, trade name, manufactured by Nippon Iron Powder Co., Ltd.) was uniformly mixed with 10 parts by mass of the toner to prepare a developing agent. As a result of conducting copying using the developing agent in a dry-type plain paper electrophotographic copier (NP-5000, trade name, manufactured by Canon Inc.), it can be seen that the toner has excellent spectral characteristics and shows excellent properties as a toner.

Example 3

Manufacture and Evaluation of Color Filter

<Manufacture of Color Filter>

(Preparation of Positive-Type Resist Composition)

3.4 parts by mass of a cresol novolak resin (mass average molecular weight 4300 in terms of polystyrene) obtained from a mixture of m-cresol/p-cresol/formaldehyde (reaction mol ratio=5/5/7.5), 1.8 parts by mass of o-naphthoquinonediazide-5-sulfonic acid ester (two hydroxyl groups being esterified on average) prepared using a phenol compound of the following formula, 0.8 parts by mass of hexamethoxy methylolated melamine, 20 parts by mass of ethyl lactate and 1 part by mass of Exemplary Compound 1 (b=0.5, c=1.5) were mixed to obtain a positive-type resist composition.

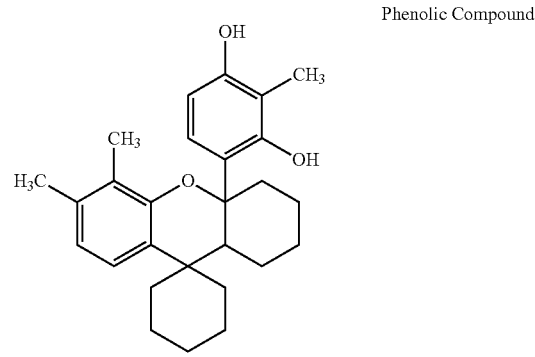 [SMILES: Cc1ccc2c(c1C)OC1(c3ccc(O)c(C)c3O)CCCCC1C21CCCCC1]

Phenolic Compound (Manufacture of Color Filter)

The obtained positive-type resist composition was spin-coated on a silicon wafer, followed by evaporating away the solvent. Subsequently, the silicon wafer was exposed through a mask, and the quinonediazide compound was decomposed. Thereafter, the wafer was heated at 100° C. and successively, the exposed portion was removed by alkali development to obtain a positive-type colored pattern having a resolution of 0.8 μm. After exposing the whole surface, the wafer was heated at 150° C. for 15 minutes to obtain a magenta complementary color-based color filter. The exposure was performed by means of an i-ray exposing stepper HITACHI LD-5010-i (trade name, manufactured by Hitachi Ltd., NA=0.40). Furthermore, as the developing solution, SOPD or SOPD-B (both trade names, manufactured by Sumitomo Chemical Co., Ltd.) was used.

The obtained color filter has good color purity and high transparency, and shows good performances.

INDUSTRIAL APPLICABILITY

According to the present invention, it is possible to provide a colorant which further improves image fastness including ozone resistance, light fastness and moisture resistance, and imparts a printed matter which is excellent in print concentration.

Although the present invention has been described in detail with reference to specific embodiments, it is obvious to those skilled in the art that various changes or modifications may be made without departing from the spirit and scope of the present invention.

This application is based on Japanese Patent Application (Japanese Patent Application No. 2011-188043) filed on Aug. 30, 2011, of which the content is incorporated herein by reference.

The invention claimed is:

1. A coloring composition comprising a compound represented by Formula (1):

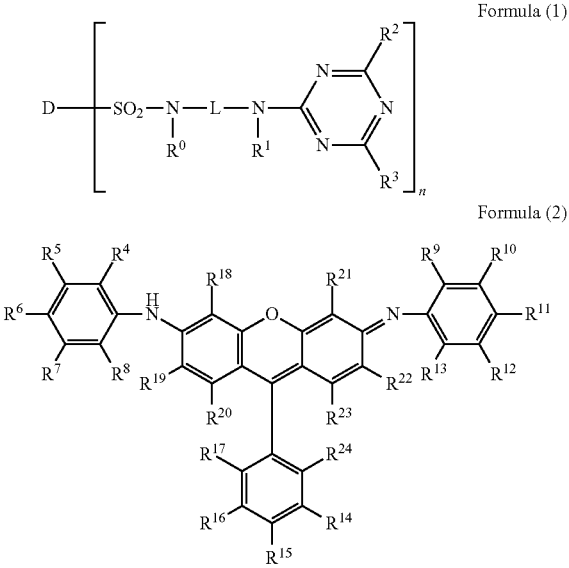

Formula (1)

Formula (2)

wherein, in Formula (1), $R^0$ to $R^3$ each independently represent a hydrogen atom or a substituent, and $R^0$ and $R^1$, $R^0$ and L, or $R^1$ and L may be combined with each other to form a ring, L represents a single bond or a divalent linking group, D represents a residue in which a hydrogen atoms are removed from a compound represented by Formula (2), n represents an integer of 1 or more, provided that when n represents an integer of 2 or more, a plurality of $R^0$'s to $R^3$'s and L's may be the same or different, the compound represented by Formula (1) has at least one ionic hydrophilic group, and in Formula (2), $R^4$ to $R^{24}$ each independently represent a hydrogen atom or a substituent.

2. The coloring composition of claim 1,
wherein in Formula (2), $R^4$, $R^8$, $R^9$ and $R^{13}$ each independently represent a hydrogen atom or an aliphatic group.

3. The coloring composition of claim 1,
wherein in Formula (2), $R^5$ to $R^7$, $R^{10}$ to $R^{12}$ and $R^{14}$ to $R^{23}$ represent a hydrogen atom.

4. The coloring composition of claim 3,
wherein in Formula (2), $R^{24}$ represents a hydrogen atom or an ionic hydrophilic group, and
in Formula (1), D represents a residue in which a hydrogen atoms are removed from hydrogen atoms as $R^5$ to $R^7$, $R^{10}$ to $R^{12}$ and $R^{24}$ of the compound represented by Formula (2), provided that n represents an integer of 1 to 7.

5. The coloring composition of claim 1,
wherein L in Formula (1) represents an alkylene group having 1 to 10 carbon atoms, which may have a substituent.

6. An inkjet ink comprising the coloring composition of claim 1.

7. An inkjet recording method comprising forming an image by using the coloring composition of claim 1.

8. An inkjet recording method comprising forming an image by using the inkjet ink of claim 6.

9. A compound represented by Formula (1):

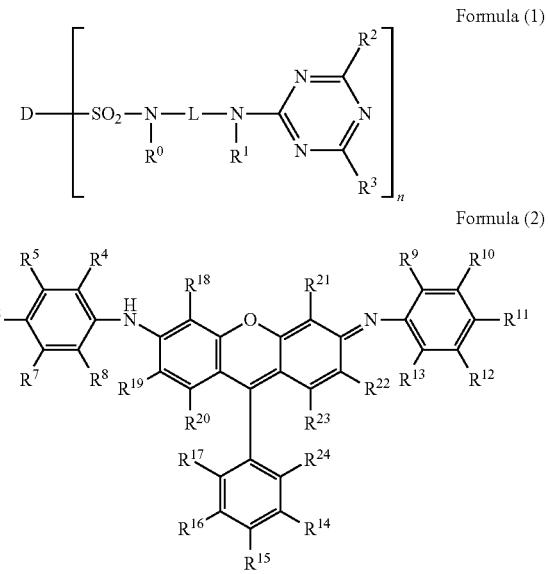

Formula (1)

Formula (2)

wherein in Formula (1), $R^0$ to $R^3$ each independently represent a hydrogen atom or a substituent, and $R^0$ and $R^1$, $R^0$ and L, or $R^1$ and L may be combined with each other to form a ring, L represents a single bond or a divalent linking group, D represents a residue in which n hydrogen atoms are removed from a compound represented by Formula (2), n represents an integer of 1 or more, provided that when a represents an integer of 2 or more a plurality of $R^0$'s to $R^3$'s and L's is optionally the same or different, the compound represented by Formula (1) has at least one ionic hydrophilic group, and in Formula (2), $R^4$ to $R^{24}$ each independently represent a hydrogen atom or a substituent.

10. A color filter comprising the compound represented by Formula (1) of claim 9.

11. A color toner comprising the compound represented by Formula (1) of claim 9.

* * * * *